(12) United States Patent
Reddy et al.

(10) Patent No.: US 12,208,108 B2
(45) Date of Patent: *Jan. 28, 2025

(54) DRUG TARGETS OF DELAYED AGING AND HUMAN BRAIN DISEASES

(71) Applicant: Texas Tech University System, Lubbock, TX (US)

(72) Inventors: Hemachandra Reddy, Lubbock, TX (US); Chandra Sekhar Kurova, Andhra Pradesh (IN)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 827 days.

This patent is subject to a terminal disclaimer.

(21) Appl. No.: 17/192,340

(22) Filed: Mar. 4, 2021

(65) Prior Publication Data

US 2021/0196732 A1    Jul. 1, 2021

Related U.S. Application Data

(63) Continuation-in-part of application No. 16/463,904, filed as application No. PCT/US2017/063485 on Nov. 28, 2017, now Pat. No. 10,987,367.

(60) Provisional application No. 62/426,956, filed on Nov. 28, 2016.

(51) Int. Cl.
| | |
|---|---|
| *A61K 31/675* | (2006.01) |
| *A61K 31/166* | (2006.01) |
| *A61K 31/517* | (2006.01) |
| *A61K 31/662* | (2006.01) |

(52) U.S. Cl.
CPC .......... *A61K 31/675* (2013.01); *A61K 31/166* (2013.01); *A61K 31/517* (2013.01); *A61K 31/662* (2013.01)

(58) Field of Classification Search
CPC .................................................. A61K 31/675
See application file for complete search history.

(56) References Cited

U.S. PATENT DOCUMENTS

| | | | |
|---|---|---|---|
| 8,048,888 B2 * | 11/2011 | Wosikowski-Buters | ............ A61P 1/00 514/266.4 |
| 8,455,477 B2 * | 6/2013 | Katz | ............ A61P 43/00 514/233.2 |
| 2014/0155471 A1 * | 6/2014 | Tieu | ............ A61P 25/28 514/44 R |

FOREIGN PATENT DOCUMENTS

| | | |
|---|---|---|
| KR | 1020160006958 | 1/2016 |
| KR | 1020160121295 | 10/2016 |
| WO | 2002/058686 A2 | 8/2002 |
| WO | 2008/074068 A1 | 6/2008 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Manczak 2011 Human Molecular Genetics, 2011, vol. 20, No. 13, pp. 2495-2509.*
Xie, Neuroscience, 2014, vol. 256, pp. 36-42.*
Manczak 2010, J Alzheimers Dis. 2010 ; 20(Suppl 2): S609-S631. doi: 10.3233/JAD-2010-100564.*
Feldman, Understanding 'Evergreening' : Making Minor Modifications Of Existing Medications To Extend Protections, Health Affairs Jun. 2022 41:6, 801-804.*
Dwivedi, Evergreening: A deceptive device in patent rights, Technology in Society 32 (2010) 324-330.*
Martin Aging, Jun. 2012, vol. 4, No. 6, 393-401.*
Baek, Journal of Neuroscience May 17, 2017, 37 (20) 5099-5110.*
Pinzi, Int. J. Mol. Sci. 2019, 20, 4331.*
Kim Biochimica et Biophysica Acta (BBA)—Molecular Cell Research, vol. 1863, Issue 11, Nov. 2016, pp. 2820-2834.*
Calkins, Marcus et al. ( Aug. 2011) Impaired mitochondrial biogenesis, defective axonal transport of mitochondria, abnormal mitochondrial dynamics and synaptic degeneration in a mouse model of Alzheimer's disease. Hum. Mol. Genet., 20, 4515-4529.
Caspersen, C. et al. (Oct. 2005) Mitochondrial Abeta: a potential focal point for neuronal metabolic dysfunction in Alzheimer's disease. FASEB J. 19, 2040-2041.
Cassidy-Stone, A. et al. (Feb. 2008) Chemical inhibition of the mitochondrial division dynamin reveals its role in Bax/Bak-dependent mitochondrial outer membrane permeabilization. Dev Cell. 14, 193-204.

(Continued)

Primary Examiner — Nizal S Chandrakumar
(74) Attorney, Agent, or Firm — Edwin S. Flores; Daniel J. Chalker; Chalker Flores, LLP

(57) ABSTRACT

The present invention includes a molecule and method of identifying and a method of using the molecule to inhibit the interaction of Aβ and Drp1 proteins, including diethyl(3,4-dihydroxyphenethylamine)(quinolin-4-yl)methylphosphonate (DDQ); phosphonium,[10-(4,5-dimethoxy-2-methyl-3,6-dioxo-1,4-cyclohexadien-1-yl)decyl]triphenyl-, methanesulfonate) (MitoQ); (3-Hydroxy-naphthalene-2-carboxylic acid (3,4-dihydroxy-benzylidene)-hydrazide (Dynasore); and/or (3-(2,4-Dichloro-5-methoxyphenyl)-2,3-dihydro-2-thioxo-4(1H)-quinazolinone, or derivatives thereof.

13 Claims, 15 Drawing Sheets

Specification includes a Sequence Listing.

(56) References Cited

OTHER PUBLICATIONS

Devi, L. et al. (Aug. 30, 2006) Accumulation of amyloid precursor protein in the mitochondrial import channels of human Alzheimer's disease brain is associated with mitochondrial dysfunction. J. Neurosci. 26, 9057-9068.
Du, H. et al (Oct. 2008) Cyclophilin D deficiency attenuates mitochondrial and neuronal perturbation and ameliorates learning and memory in Alzheimer's disease. Nat. Med. 14, 1097-1105.
Du, H. et al. (Oct. 26, 2010) Early deficits in synaptic mitochondria in an Alzheimer's disease mouse model. Proc Natl Acad Sci U S A. 107, 18670-18675.
Du, H. et al. (2012) Synaptic mitochondrial pathology in Alzheimer's disease. Antioxid Redox Signal. 16, 1467-1475.
Gouras, G.K. et al. (May 2005) Intraneuronal Abeta accumulation and origin of plaques in Alzheimer's disease. Neurobiol. Aging. 26, 1235-1244.
Gouras, GK et al. (Jan. 1, 2000) Intraneuronal Abeta-42 accumulation in human brain. Am J Pathol. 156, 15-20.
Gouras, GK et al. (May 2010) Intraneuronal beta-amyloid accumulation and synapse pathology in Alzheimer's disease. Acta Neuropathol. 119, 523-541.
Hansson, Petersen CA et al. (Sep. 2, 2008) The amyloid beta-peptide is imported into mitochondria via the TOM import machinery and localized to mitochondrial cristae. Proc Natl Acad Sci U S A. 105, 13145-13150.
International Search Report and Written Opinion, PCT/US2017/063485 [ISA/AU] dated Jan. 9, 2018.
Kacprzak, V. et al. Dopaminergic control of anxiety in young and aged zebrafish. Pharmacol Biochem Behav. Jun. 2017. pii: S0091-3057(16)30212-X.
Kandimalla, R. et al. (Dec. 2016) Multiple faces of dynamin-related protein 1 and its role in Alzheimer's disease pathogenesis. Biochim Biophys Acta. 1862, 814-828.
Kandimalla, R. et al. (Sep. 2016) Reduced dynamin-related protein 1 protects against phosphorylated Tau-induced mitochondrial dysfunction and synaptic damage in Alzheimer's disease. Hum Mol Genet. 25, 4881-4897.
Kuruva, CS et al. (Feb. 2017) Amyloid beta modulators and neuroprotection in Alzheimer's disease: a critical appraisal, Drug Discov Today. 2, 223-233.
Laferla, FM et al. (Jul. 2007) Intracellular amyloid-beta in Alzheimer's disease. Nat Rev Neurosci. 8, 499-509.
Li, YJ et al. (Aug. 13, 2015) Novel Coumarin-Containing Aminophosphonatesas Antitumor Agent: Synthesis, Cytotoxicity, DNA-Binding and Apoptosis Evaluation. Molecules. 20, 14791-14809.
Li, Zheng et al. (Dec. 17, 2004) The importance of dendritic mitochondria in the morphogenesis and plasticity of spines and synapses. Cell. 119(6):873-87.
Lustbader, JW et al. (Apr. 16, 2004) ABAD directly links Abeta to mitochondrial toxicity in Alzheimer's disease. Science. 304, 448-452.
Macia E, et al. (Jun. 2006) Dynasore, a cell-permeable inhibitor of dynamin. Dev Cell. 10, 839-850.
Manczak, M. et al. (Mar. 2006) Mitochondria are a direct site of A beta accumulation in Alzheimer's disease neurons: implications for free radical generation and oxidative damage in disease progression. Hum Mol Genet. 15, 1437-1449.
Manczak, M. et al. (Feb. 2012) Abnormal interaction between the mitochondrial fission protein Drp1 and hyperphosphorylated tau in Alzheimer's disease neurons: implications for mitochondrial dysfunction and neuronal damage. Hum Mol Genet. 21, 2538-2547.
Manczak, M. et al. (Aug. 2012) Abnormal interaction of VDAC1 with amyloid beta and phosphorylated tau causes mitochondrial dysfunction in Alzheimer's disease. Hum Mol Genet. 21, 5131-5146.
Manczak, M. et al. (Sep. 2016) Protective effects of reduced dynamin-related protein 1 against amyloid beta-induced mitochondrial dysfunction and synaptic damage in Alzheimer's disease. Hum Mol Genet. Hum Mol Genet 25, 5148-5166.
Manczak, M. et al. (Mar. 2011) Impaired mitochondrial dynamics and abnormal interaction of amyloid beta with mitochondrial protein Drp1 in neurons from patients with Alzheimer's disease: implications for neuronal damage. Hum Mol Genet. 20, 2495-2509.
Manczak, Maria et al. (2010) Mitochondria-targeted antioxidants protect against amyloid-beta toxicity in Alzheimer's disease neurons. J. Alzheimers Dis., 20(Suppl. 2), S609-S631.
Mattson, MP (Aug. 5, 2004) Pathways towards and away from Alzheimer's disease. Nature. 430, 631-639.
Ordonez, M. et al. (Jan. 3, 2009) An overview of stereoselective synthesis of α-aminophosphonic acids and derivatives. Tetrahedron. 65, 17-49.
Reddy, P.H. et al. (Oct. 2012) Abnormal mitochondrial dynamics and synaptic degeneration as early events in Alzheimer's disease: implications to mitochondria-targeted antioxidant therapeutics. Biochim. Biophys. Acta, 1822, 639-649.
Reddy, PH (2006) Amyloid precursor protein-mediated free radicals and oxidative damage: implications for the development and progression of Alzheimer's disease. J Neurochem. 96, 1-13.
Reddy, PH (Aug. 2009) Amyloid beta, mitochondrial structural and functional dynamics in Alzheimer's disease. Exp Neurol. 218, 286-292.
Reddy, PH et al. (Feb. 2008) Amyloid beta, mitochondrial dysfunction and synaptic damage: implications for cognitive decline in aging and Alzheimer's disease. Trends Mol Med. 14, 45-53.
Reddy, PH et al. (Mar. 2010) Amyloid-beta and mitochondria in aging and Alzheimer's disease: implications for synaptic damage and cognitive decline. J Alzheimers Dis. 20, S499-512.
Reddy, PH et al. (Jun. 24, 2011) Dynamin-related protein 1 and mitochondrial fragmentation in neurodegenerative diseases. Brain Res Rev. 67, 103-118.
Reddy, PH et al. (May 25, 2017) Mitochondria-Division Inhibitor 1 Protects Against Amyloid-β induced Mitochondrial Fragmentation and Synaptic Damage in Alzheimer's Disease J Alzheimer Dis.
Reddy, PH et al. (Feb. 2017) Mitochondria-targeted small molecule SS31: a potential candidate for the treatment of Alzheimer's disease. Hum Mol Genet doi: 10.1093/hmg/ddx052, Advance Access Publication Date: Feb. 10, 2017.
Reddy, PH (Sep. 30, 2011) Abnormal tau, mitochondrial dysfunction, impaired axonal transport of mitochondria, and synaptic deprivation in Alzheimer's disease. Brain Res. 1415, 136-148.
Sekhar, Kuruva KC, et al. (May 2014) Amino acid esters substituted phosphorylated emtricitabine and didanosine derivatives as antiviral and anticancer agents. Appl Biochem Biotechnol. 173, 1303-1318.
Selkoe, DJ (Apr. 2001) Alzheimer's disease: genes, proteins, and therapy. Physiol Rev. 81, 741-766.
Sheng, JH et al. (Apr. 2012) The peripheral messenger RNA expression of glycogen synthase kinase-3β genes in Alzheimer's disease patients: a preliminary study. Psychogeriatrics. 12, 248-254.
Swerdlow, RH et al. (2010) The Alzheimer's disease mitochondrial cascade hypothesis. J Alzheimers Dis. 20 Suppl 2:S265-279.
Swerdlow, RH (2012) Mitochondria and cell bioenergetics: increasingly recognized components and a possible etiologic cause of Alzheimer's disease. Antioxid Redox Signal. 16, 1434-1455.
Wang, X. et al. (Jul. 15, 2009) Impaired balance of mitochondrial fission and fusion in Alzheimer's disease. J. Neurosci. 29, 9090-9103.
Wang, Xinglong et al. (Dec. 9, 2008) Amyloid-beta overproduction causes abnormal mitochondrial dynamics via differential modulation of mitochondrial fission/fusion proteins. Proc. Natl. Acad. Sci. USA., 105, 19318-19323.
Yao, J et al. (Aug. 25, 2009) Mitochondrial bioenergetic deficit precedes Alzheimer's pathology in female mouse model of Alzheimer's disease. Proc Natl Acad Sci U S A. 106, 14670-14675.
Zhu, Z et al. (Aug. 7, 2013) Arctigenin effectively ameliorates memory impairment in Alzheimer's disease model mice targeting both β-amyloid production and clearance. J Neurosci. 33, 13138-13149.
Xie, N. et al., "Inhibition of Mitochondrial Fission Attenuates Aβ-induced Microglia Apoptosis", Neuroscience, 2014, vol. 256, pp. 36-42.

(56) References Cited

OTHER PUBLICATIONS

Pradeep, H. et al. "Computational Prediction of a Putative Binding Site on Drp1: Implications for Antiparkinson Therapy", Journal of Chemical Information and Modelling, 2014, vol. 54, pp. 2042-2050.
Kuruva, C. S. et al., "Aqua-Soluble DDQ Reduces the Levels of Drp1 and Aβ and Inhibits Abnormal Interactions Between Aβ and Drp1 and Protects Alzheimer's Disease Neurons from Aβ-and Drp1-Induced Mitochondrial and Synaptic Toxicities", Human Molecular Genetics, 2017, vol. 26, No. 17, pp. 3375-3395.

* cited by examiner

1. CELLS + ABETA42 - IP
2. CELLS + ABETA42 + DDQ - IP
3. CELLS + DDQ + ABETA42 - IP
4. CELLS + ABETA42 - LYSATE
5. CELLS + ABETA42 + DDQ - LYSATE
6. CELLS + DDQ + ABETA42 - LYSATE

1. CELLS + ABETA42 - IP
2. CELLS + ABETA42 + DDQ - IP
3. CELLS + DDQ + ABETA42 - IP
4. CELLS + ABETA42 - LYSATE
5. CELLS + ABETA42 + DDQ - LYSATE
6. CELLS + DDQ + ABETA42 - LYSATE

DRUG TARGETS OF DELAYED AGING AND HUMAN BRAIN DISEASES

CROSS-REFERENCE TO RELATED APPLICATIONS

This application is a continuation in part application of U.S. patent application Ser. No. 16/463,904, filed on May 24, 2019 and which claims priority to and is a U.S. National Stage Patent Application of International Application No. PCT/US2017/063485, filed Nov. 28, 2017, which claims priority to U.S. Patent Appl. Ser. No. 62/426,956, filed Nov. 28, 2016. The foregoing patent applications are hereby incorporated by reference herein in their entirety for all purposes.

STATEMENT OF FEDERALLY FUNDED RESEARCH

This invention was made with government support under AG042178 awarded by the National Institutes on Aging. The government has certain rights in the invention.

TECHNICAL FIELD OF THE INVENTION

The present invention relates generally to tryptamine, dopamine and quinolone derivatives and their use in delay aging and diseases of the human brain. The composition and methods use such a compound and may also be used in combination with a potentiator to delay aging.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on Nov. 27, 2017, is named TECH2009WO_SeqList and is 8 kilobytes in size.

BACKGROUND OF THE INVENTION

Without limiting the scope of the invention, its background is described in connection with neurological conditions. The World Alzheimer's Report estimated that in 2015, 47.5 million people had AD-related dementia ("dementia") worldwide, and these numbers were expected to rise to 75.6 million by 2030 and to 131.5 million by 2050. Over 9.9 million new cases of AD-related dementia are diagnosed every year worldwide, which translates to 1 new case every 3.2 seconds. In high-income countries, such as the United States and Germany, seven in 10 persons aged 70 years and older will pass away with some form of dementia. Dementia has a huge economic impact on society, on the persons with dementia, and on their families and caretakers. The estimated total healthcare cost of dementia worldwide in 2015 was estimated at $818 billion, and the World Alzheimer's Report foresees dementia as a trillion-dollar disease by 2018.

While scientists are trying to determine causes of Alzheimer's Disease ("AD"), they have pinpointed several cellular changes that increase a person's risk for developing it, including synaptic loss and dysfunction, Aβ production and accumulation, inflammatory responses, phosphorylated tau formation and accumulation, cell cycle deregulation, and hormonal imbalance. Aging is the number one risk factor for AD. Mounting evidence indicates that Aβ plays a key role in AD pathophysiology. Intra-neuronal Aβ and Aβ deposits early in the disease process, and intracellular hyperphosphorylated tau and neurofibrillary tangles later in the disease process, have been found in postmortem brains from AD patients. In addition, Aβ has been found to induce synaptic dysfunction and mitochondrial oxidative damage, resulting in abnormal activation of redox-mediated events, as well as an abnormal elevation of cytoplasmic $Ca^{2+}$, ultimately causing neuronal damage. AD pathogenesis has been linked to DNA damage. In mammals, including humans, an accumulation of oxidative DNA damage in particularly mutant DNA, including brain tissue, has been found in aging persons.

One example is Patent Application Publication No. WO2008/074068, entitled, "Substituted quinoline derivatives as antiamyloidogeneic agents," discloses heterocyclic compounds, processes for their preparation and their use as pharmaceutical or veterinary agents, in particular for the treatment, amelioration and/or prophylaxis of conditions caused by or associated with unbalanced metal levels and/or oxidative stress, such as neurological conditions and cellular proliferative disorders, for example Alzheimer's disease, Parkinson's disease, Huntington's disease or brain cancer or tumors.

Another example is Patent Application Publication No. WO2002/058686, entitled, "Method of treatment of neurodegenerative disorders using pentaaza-macrocyclic ligand complexes," discloses pharmaceutical compositions and methods using such compositions for the treatment of neurodegenerative disorders. Such compositions contain a catalyst for the dismutation of superoxide, including superoxide dismutase enzyme (SOD) and low molecular weight organic ligand derived metal complexes that function as mimics of the enzyme (SOD mimetics or SODms).

SUMMARY OF THE INVENTION

The inventors designed a number of molecules with the aid of molecular docking software to reduce/prevent interactions between Aβ and Drp1; 9 Aβ and p-tau; 24 Aβ and VDAC129. Specifically, the inventors implemented the use of four distinct scaffolding structures with molecular docking simulation to fit the active sites of each enzyme and extrapolate R-groups with high binding affinity against abnormal protein interactions. Thus, the present invention includes methods for identifying molecules that can delay aging process and prevent and/or stop neurodegeneration. The inventors discovered molecules that cause delayed aging and protect cells from oxidative insults. The inventors also identified specific molecule that can be modified to increase their effectiveness, and methods for using the same to treat neurodegenerative disease. It was found that the molecules possess certain features, e.g., (1) delayed aging, (2) protect human cells from oxidative insults, (3) reduce the toxicity of mutant proteins, (4) inhibit abnormal protein interactions in the brain cells, and/or (5) enhance cell survival.

In one embodiment, the present invention includes a molecule that inhibits the interaction of Aβ and Drp1 proteins. In one aspect, the molecule inhibits the interaction of Aβ and Drp1 proteins in nerve cells. In another aspect, the molecule inhibits mitochondrial, intracellular, and extracellular damage caused by the interaction of Aβ and Drp1 in or about nerve cells. In another aspect, the molecule is water-soluble. In another aspect, the molecule is adapted for oral, intravenous, intramuscular, intraperitoneal, subcutaneous, parenteral, or pulmonary administration. In another aspect, the Aβ and Drp1 proteins are human. In another aspect, the molecule delays age-dependent disease process in Alzheimer's, Huntington's, Parkinson's and ALS. In another aspect, the molecule at least one of: delays aging in neurons, protects neurons from oxidative insults, inhibits abnormal protein-protein interactions and protect neurons from mutant protein(s)-induced toxicities, and enhances cell survival. In another aspect, the molecule is selected from at least one of: phosphonium cation-based structures; quinoline based alpha aminophosphonates; napthaline based alpha aminophosphonates, or hexahydropyramidine carboxylates structures. In another aspect, the composition is selected from at least one of:

DDQ (diethyl(3,4-dihydroxyphenethylamine)(quinolin-4-yl)methylphosphonate):

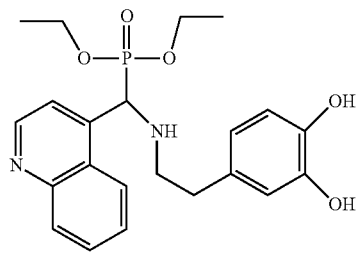 [SMILES: CCOP(=O)(OCC)C(NCCc1ccc(O)c(O)c1)c1ccnc2ccccc12]

MitoQ: (Phosphonium, [10-(4,5-dimethoxy-2-methyl-3,6-dioxo-1,4-cyclohexadien-1-yl)decyl]triphenyl-, methanesulfonate), shown here in the non-limiting form of a mesylate.

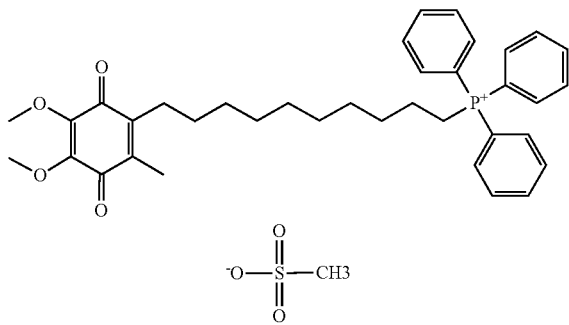

Dynasore: (3-Hydroxy-naphthalene-2-carboxylic acid (3,4-dihydroxy-benzylidene)-hydrazide) shown here in the non-limiting form of a hydrate:

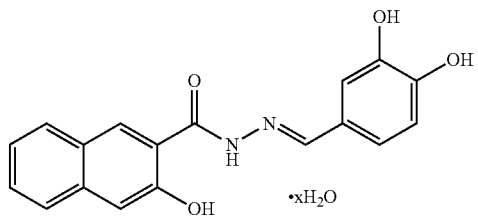 [SMILES: O=C(N/N=C/c1ccc(O)c(O)c1)c1cc2ccccc2cc1O]

Mdiv-1: (3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone):

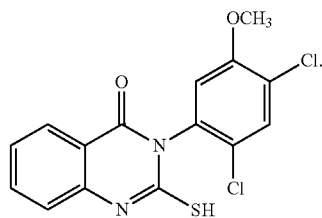 [SMILES: COc1cc(-n2c(S)nc3ccccc3c2=O)c(Cl)cc1Cl]

In another aspect, the shaded regions are modified to at least one of: increase the inhibition of Aβ and Drp1 binding, increase crossing the blood-brain-barrier, increase solubility, or increase the metabolic half-life of the molecule.

Another embodiment of the present invention includes a method for identifying a molecule that inhibits the interaction of Aβ and Drp1 proteins comprising: obtaining a database of molecular coordinates for the regions of the Aβ and Drp1 proteins that interact; obtaining a database of molecules comprising molecular coordinates; identifying the molecules from the database of molecules that fit between the regions in which the Aβ and Drp1 proteins that interact; and testing in vitro the ability of the one or more molecules that fit between the regions in which the Aβ and Drp1 proteins to prevent binding of Aβ and Drp1 proteins. In one aspect, the method further comprises testing the inhibition of the one or more molecules to inhibit the interaction of Aβ and Drp1 proteins in nerve cells. In another aspect, the method further comprises testing the molecule to inhibit mitochondrial, intracellular, and extracellular damage caused by the interaction of Aβ and Drp1 in or about nerve cells. In another aspect, the molecule is water soluble. In another aspect, the method further comprises adapting the molecule for oral, intravenous, intramuscular, intraperitoneal, subcutaneous, parenteral, or pulmonary administration. In another aspect, the method further comprises testing the one or more molecules to delay age-dependent disease process in Alzheimer's, Huntington's, Parkinson's and ALS. In another aspect, the one or more molecules at least one of: delays aging in neurons, protects neurons from oxidative insults, inhibits abnormal protein-protein interactions and protect neurons from mutant protein(s)-induced toxicities, and enhances cell survival. In another aspect, the method further comprises selecting from at least one of: phosphonium cation based structures; quinoline based alpha aminophosphonates; napthaline based alpha aminophosphonates, or hexahydropyramidine carboxylates structures. In another aspect, the molecule tested is, or is based on, at least one of:

DDQ (diethyl(3,4-dihydroxyphenethylamine)(quinolin-4-yl)methylphosphonate):

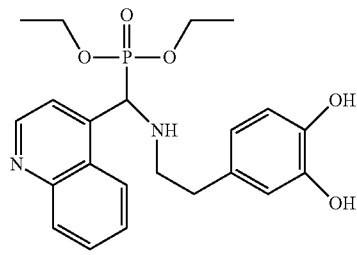 [SMILES: CCOP(=O)(OCC)C(NCCc1ccc(O)c(O)c1)c1ccnc2ccccc12]

MitoQ: (Phosphonium, [10-(4,5-dimethoxy-2-methyl-3,6-dioxo-1,4-cyclohexadien-1-yl)decyl]triphenyl-, methanesulfonate), shown here in the non-limiting form of a mesylate.

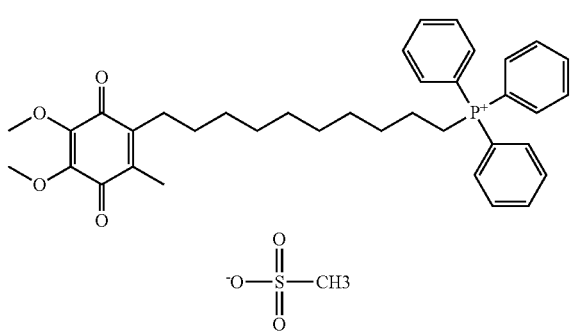

Dynasore: (3-Hydroxy-naphthalene-2-carboxylic acid (3,4-dihydroxy-benzylidene)-hydrazide) shown here in the non-limiting form of a hydrate:

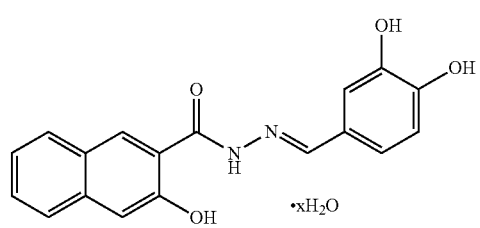 [SMILES: O=C(N/N=C/c1ccc(O)c(O)c1)c1cc2ccccc2cc1O]

Mdivi-1: (3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone):

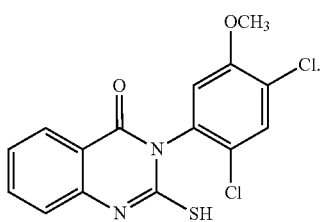 [SMILES: COc1cc(-n2c(S)nc3ccccc3c2=O)c(Cl)cc1Cl]

In another aspect, the shaded regions are modified to at least one of: increase the inhibition of Aβ and Drp1 binding, increase crossing the blood-brain-barrier, increase solubility, or increase the metabolic half-life of the molecule.

Yet another embodiment of the present invention includes a method of treating a neuropathy caused by the interaction of Aβ and Drp1 proteins comprising providing a molecule that inhibits the interaction of the Aβ and Drp1 proteins. In one aspect, the molecule inhibits the interaction of Aβ and Drp1 proteins in nerve cells. In another aspect, the molecule inhibits mitochondrial, intracellular, and extracellular damage caused by the interaction of Aβ and Drp1 in or about nerve cells. In another aspect, the molecule is water soluble. In another aspect, the molecule is adapted for oral, intravenous, intramuscular, intraperitoneal, subcutaneous, parenteral, or pulmonary administration. In another aspect, the Aβ and Drp1 proteins are human. In another aspect, the neuropathy is an age-dependent disease selected from Alzheimer's, Huntington's, Parkinson's disease or ALS. In another aspect, the molecule at least one of: delays aging in neurons; protects neurons from oxidative insults; inhibits abnormal protein-protein interactions and protect neurons from mutant protein(s)-induced toxicities; and enhances cell survival. In another aspect, the molecule is selected from at least one of: phosphonium cation-based structures; quinoline based alpha aminophosphonates; napthaline based alpha aminophosphonates, or hexahydropyramidine carboxylates structures. In another aspect, the molecule is, or is based on, at least one of:

DDQ (diethyl(3,4-dihydroxyphenethylamine)(quinolin-4-yl)methylphosphonate):

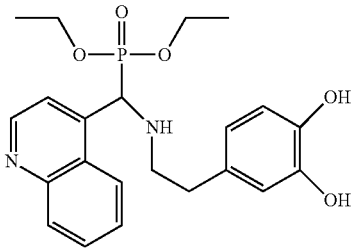 [SMILES: CCOP(=O)(OCC)C(NCCc1ccc(O)c(O)c1)c1ccnc2ccccc12]

MitoQ: (Phosphonium, [10-(4,5-dimethoxy-2-methyl-3,6-dioxo-1,4-cyclohexadien-1-yl)decyl]triphenyl-, methanesulfonate), shown here in the non-limiting form of a mesylate.

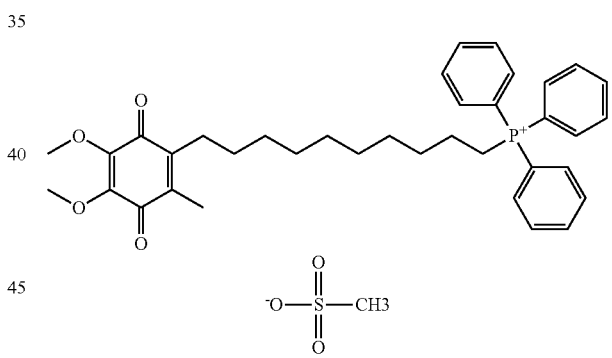

Dynasore: (3-Hydroxy-naphthalene-2-carboxylic acid (3,4-dihydroxy-benzylidene)-hydrazide) shown here in the non-limiting form of a hydrate:

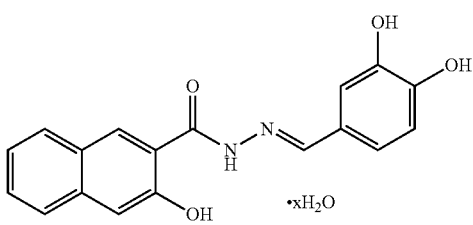 [SMILES: O=C(N/N=C/c1ccc(O)c(O)c1)c1cc2ccccc2cc1O]

Mdivi-1: (3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone):

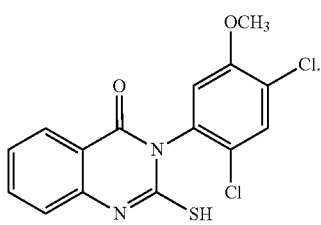 [SMILES: COc1cc(-n2c(S)nc3ccccc3c2=O)c(Cl)cc1Cl]

In another aspect, the shaded regions are modified to at least one of: increase the inhibition of Aβ and Drp1 binding, increase crossing the blood-brain-barrier, increase solubility, or increase the metabolic half-life of the molecule.

BRIEF DESCRIPTION OF THE DRAWINGS

For a more complete understanding of the features and advantages of the present invention, reference is now made to the detailed description of the invention along with the accompanying figures and in which:

FIG. 1A. Interaction of Drp1 (PDB ID: 4h1u) and Aβ1-40 (PDBID: 1ba4) proteins. FIG. 1B. Inhibition of Drp1 and Aβ40 peptide Interaction by DDQ. FIG. 1C. Interaction of Drp1 and designed drug molecules. The inventors designed 82 molecules based on existing mitochondrial division inhibiting drug molecules in AD and subjected to molecular docking studies. The inventors prepared Aβ and Drp1 complex and introduced these molecular structures into this complex. Few of these molecules showed better docking score compared to existed drug molecules. Amongst DDQ is only involved in the prevention of Aβ-Drp1 interaction by interacting at the active site such as ser8 and Leu34 of Aβ and ASN16 Glu16 of Drp1. And also DDQ showed better binding score (−10.8462) than existed drug molecules. DDQ is readily stopping the Drp1 before forming the complex. DDQ exhibited binding interaction at Arg225 (C═O→O— P) and phenyl part of DDQ is also showing one arene cationic interaction at Arg225. Hence, among all designed molecules the inventors selected DDQ for detailed analysis but the methods and techniques apply equally to the four compounds without undue experimentation.

As shown in FIG. 3, the inventors studied five different groups of cells: (1) untreated SHSY5Y cells; (2) SHSY5Y cells treated (incubated) with DDQ (250 nM) for 24 hours; (3) SHSY5Y cells incubated with the Aβ1-42 peptide (20 μM final concentration) for 6 hours; (4) SHSY5Y cells incubated with Aβ1-42 for 6 hours, followed by DDQ treatment for 24 hours, and (5) SHSY5Y cells treated with DDQ for 24 hours, followed by Aβ1-42 incubation for 6 hours.

FIG. 4A. Representative Immunoblotting images (mitochondrial fission, fusion proteins and synaptic proteins) of DDQ, Aβ+DDQ and DDQ+Aβ treated and untreated SHSY-5Y cells. FIG. 4B. Representative Immunoblotting images (mitochondrial biogenesis proteins) of DDQ, Aβ+DDQ and DDQ+Aβ treated and untreated SHSY-5Y cells. FIG. 4C. Quantitative densitometry analysis of mitochondrial dynamics and synaptic proteins. Quantitative densitometry analysis of mitochondrial biogenesis. Fission proteins levels were increased in cells treated with Aβ; and reduced in cells treated with DDQ, Aβ+DDQ and DDQ+Aβ treated cells. Whereas mitochondrial fusion proteins Mfn1 and Mfn2 and synaptic proteins, synaptophysin and PSD95 were decreased in cells treated with Aβ, and enhanced in cells treated with DDQ, Aβ+DDQ and DDQ+Aβ treated cells.

FIG. 5A shows immunoprecipitation with the 6E10 antibody and immunoblotting with the 6E10 antibody, indicating that the specificity of 6E10 in the Co-IP analysis. In cells treated with DDQ+Aβ and Aβ+DDQ, 4 kDa Aβ levels were reduced relative cells treated Aβ alone. FIG. 5B shows Co-IP with Aβ antibody 6E10 and western blotting with Drp1 antibody, indicating that Drp1 interacts with 4 kDa Aβ. Reduced interaction between Aβ and Drp1 was found in cells pretreated with DDQ and then Aβ added. Reduced interaction was strong in DDQ+Aβ cells compared to cells treated with Aβ alone.

FIG. 7A shows representative immunofluorescence images of mitochondrial dynamic proteins and synaptic proteins. FIG. 7B shows quantitative immunofluorescence analysis of mitochondrial dynamics and synaptic proteins.

As shown in FIGS. 7A and 7B, increased levels of Drp1 and intra-neuronal Aβ (full-length APP) and colocalization of Drp1 and Aβ in top panel, where as in the middle panel Aβ+DDQ cells, reduced Drp1 and Aβ and also reduced colocalization and in the bottom panel Drp1 and Aβ levels markedly reduced compared to top panel and also colocalization of Drp1 and Aβ. These findings strongly suggest that DDQ 1) reduces Drp1 and Aβ levels and also 2) inhibit the interaction of Drp1 and Aβ in SHSY5Y cells. These findings agree with the Co-IP findings.

FIG. 9A shows Aβ42 and FIG. 9B shows Aβ40. Significantly reduced levels of Aβ42 in mutant APPSwe/Ind cells treated with DDQ compared to mutant APPSwe/Ind cells untreated with DDQ. On the contrary, Aβ40 levels were significantly increased in mutant APPSwe/Ind cells treated with DDQ relative to mutant APPSwe/Ind cells untreated with DDQ.

DETAILED DESCRIPTION OF THE INVENTION

Figure 1A:
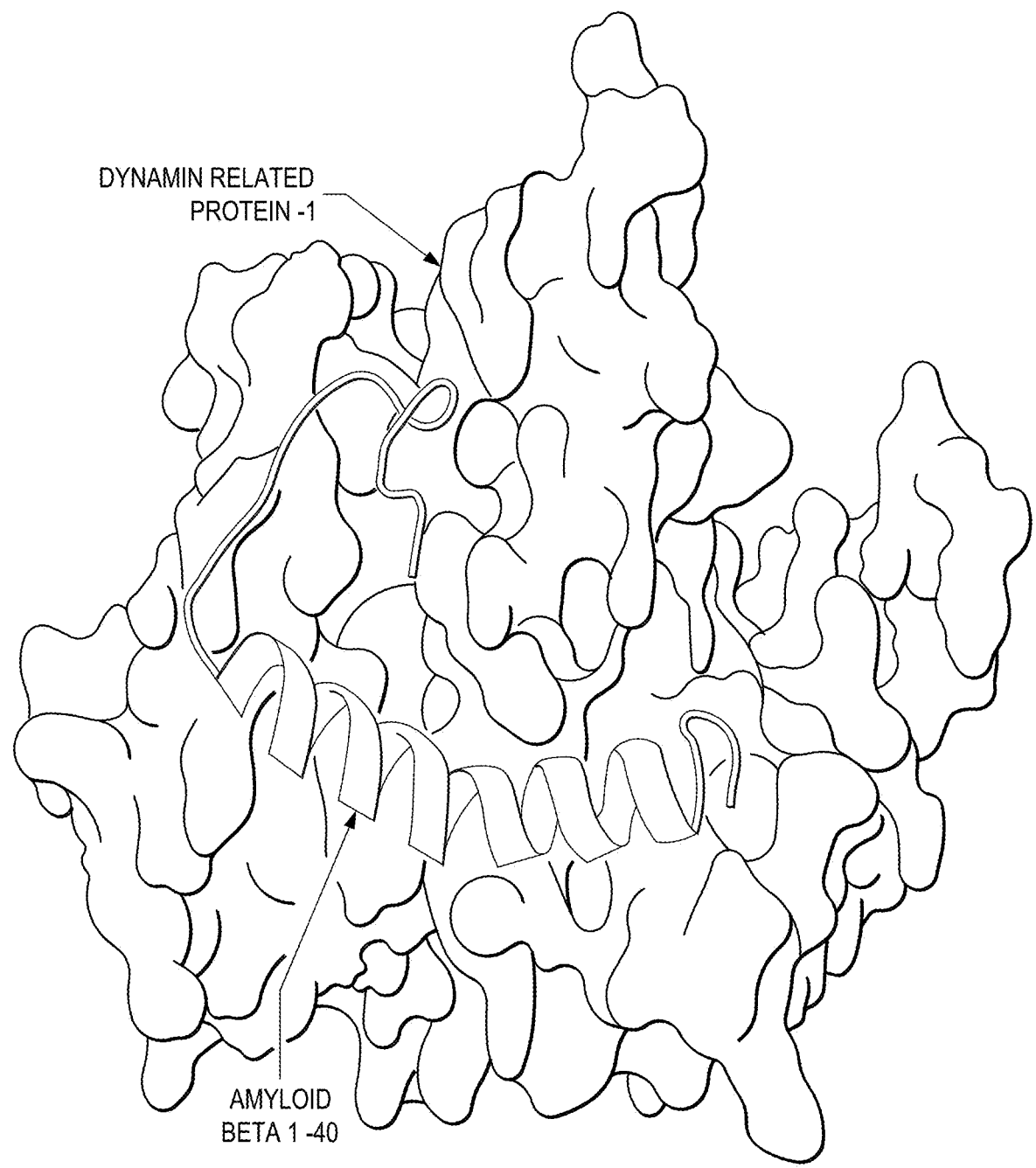
FIGS. 1A to 1C show the interaction of designed drug molecules against Aβ and Drp1 Complex.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

An arising characteristic of neurodegenerative disease is the improper regulation of proteins responsible for mitochondrial fusion, fission, localization, membrane transport, and more in neurons. Recent research by the inventors has revealed the critical role of various enzymes specifically as mitochondrial regulators, including amyloid-β (Aβ), dynamin-related protein 1 (Drp1), phosphorylated tau (p-tau), and voltage-dependent anion channel protein 1 (VDAC1). The inventors have shown that interactions between combinations of these enzymes contribute to mitochondrial dysfunction and bioenergetic compromise that may cause neurodegeneration.

The present invention includes methods for identifying molecules that can delay aging process and prevent and/or stop neurodegeneration and novel compositions that delay aging and protect cells from oxidative insults, and method of using the same. It was found that the molecules identified were able to: (1) delay aging, (2) protect human cells from oxidative insults, (3) reduce the toxicity of mutant proteins, (4) inhibit abnormal protein interactions in the brain cells and (5) enhance cell survival. To date, no drugs have been developed to prevent and/or reduce abnormal protein interactions in Alzheimer's, Huntington's, and Parkinson's. The newly developed molecules inhibit these abnormal interactions and enhance cell survival and delay aging process.

Neurons are the building blocks of the nervous system, which includes the brain and spinal cord. Neurons normally don't reproduce or replace themselves, so when they become damaged or die they cannot be replaced by the body. Examples of neurodegenerative diseases are Alzheimer's, Huntington's disease, Parkinson's and amyotrophic lateral sclerosis (ALS). Various factors such as pathogenic mutations, genetic modifiers, abnormal interactions between disease causing proteins such amyloid beta or Aβ (in Alzheimer's), mutant huntingtin (in Huntington's), mutant SOD1 (in ALS) and parkin, DJ1 (in Parkinson's) and other diet and metabolism. In addition, aging is a major risk factor for neurodegenerative diseases.

Especially, in brain cells strong evidence indicates the amyloid beta precursor protein (APP), is the source of Aβ, the central player in the pathophysiology of the disease. This released Aβ induces synaptic dysfunction, mitochondrial oxidative damage, resulting in abnormal activation of redox-mediated events as well as elevation of cytoplasmic Ca2+, ultimately causing neuronal damage in AD. Recent evidence from our lab suggests mutant AD proteins Aβ and phosphorylated tau interacts mitochondrial fission protein, dynamin-related protein 1 (Drp1), induces mitochondrial fragmentation, mitochondrial dysfunction and synaptic damage in AD neurons. These abnormal interactions are age, mutant protein and disease progression dependent, indicating that age aging and abnormal protein interactions play a key role in AD development and pathogenesis. More recently, the present inventors found that mutant AD proteins Aβ and phosphorylated interacts with mitochondrial outer-membrane protein, voltage-dependent anion channel protein 1 (VDAC1), blocks mitochondrial permeability transition pores and causes gating of mitochondrial pore activities, ultimately leading to impairments in oxidative phosphorylation and low ATP production in AD neurons9. These abnormal protein-protein interactions lead to mitochondrial dysfunction, bioenergetics compromise and consequent synaptic dysfunction and loss and neuronal dysfunction in AD.

In AD, Aβ-induced synaptic dysfunction is a complicated process involving multiple pathways, components, and biological events, such as oxidative stress, kinase activation, and protein interactions. These complexities lead to the formation and accumulation of Aβ and phosphorylated tau, mitochondrial dysfunction, and ultimately neuronal death. Despite the numbers of clinical trials conducted to identify drug targets (i.e., molecules) that may reduce mutant protein toxicity in AD, such molecules remain unidentified. Recent research established that synaptic damage and mitochondrial dysfunction are early events in AD pathogenesis. Mitochondrial dysfunction is mainly due to the abnormal interaction of Drp1 with Aβ, and with phosphorylated tau. Development of drugs capable of targeting underlying mechanisms of disease pathogenesis is needed in order to slow AD progression. The major focus of the proposed research effort is to develop a drug that can target the toxicity in involved in these interactions in order to prevent mitochondrial dysfunction and synaptic damage in AD progression.

Aβ, mitochondrial dysfunction, and AD: Extracellular canonical localization of Aβ has been identified in different subcellular compartments, including the endoplasmic reticulum; the Golgi apparatus (or the trans-Golgi network); early, late, and recycling endosomes; and the lysosome, where the Aβ are generated. In studies of postmortem brains from both AD patients and mouse models of AD, Aβ has also been found in mitochondria, and research from different independent research groups has clearly established that Aβ progressively accumulates in the mitochondria. Aβ has been found to induce mitochondrial dysfunction via different mechanisms. Aβ is taken up by mitochondria via the translocase of the outer membrane (TOM) complex and is imported into the inner membrane; Aβ alters the enzyme activity of the respiratory chain complexes I, and IV; Aβ affects mitochondrial dynamics by an impaired balance of fission and fusion; Aβ impairs mitochondrial permeability transition pore gating via the interaction of Aβ with VDAC1; Aβ induces decreased mitochondrial respiration; Aβ affects new mitochondrial biogenesis; and Aβ increases reactive oxygen species (ROS) generation.

Recent studies have shown that Drp1, which maintains and remodels mammalian mitochondria, interacts with Aβ and phosphorylates tau, leading to excessive mitochondrial fragmentation, impaired axonal transport of mitochondria, and ultimately neuronal damage and cognitive decline.

Drp1 structure and function: Based on published studies and NCBI databases, the human Drp1 has been found to have several splice variants: variant 1 consists of 736 amino acids; in variant 2, exon 15 is spliced out; in variant 3, exons 15 and 16 are spliced out and have a total of 699 amino acids; variant 4 has 725 amino acids; variant 5, 710 amino acids; and variant 6, 749 amino acids. Drp1 contains a highly conserved GTPase and is involved in various cellular functions. Similar to the human Drp1, the mouse Drp1 has been found in multiple variants: variant 1 consists of 712 amino acids; in variant 2, exon 3 is spliced out; and in variant 3, exons 15 and 16 are spliced out. Recent research findings suggest that Drp1 is involved in mitochondrial division, mitochondrial distribution, peroxisomal fragmentation, phosphorylation, SUMOlyation, and ubiquitination.

Drp1 expression and mitochondrial dysfunction: Studies of Drp1 in mammalian cells suggest that normal expression of Drp1 is critical for normal mitochondrial dynamics and normal mitochondrial distribution and dendritic morphology in neurons. In AD and other neurodegenerative diseases, Drp1 levels are altered via the interaction of Drp1 with Aβ, leading to abnormal mitochondrial dynamics (increased fission and reduced fusion), in some cases with perinuclear clusters of mitochondria and disruption of inter-mitochondrial connectivity.

Drp1 associated with Aβ: The present inventors have shown that mutant AD proteins, Aβ, and phosphorylated tau interact with Drp1, which induces mitochondrial fragmentation, mitochondrial dysfunction, and synaptic damage in neurons. These abnormal interactions are believed to be age- and disease-progression dependent, indicating that the interaction between aging and disease progression may play key roles in AD pathogenesis and development. Increasing evidence suggests that in AD, the accumulation of Aβ in synapses and synaptic mitochondria causes synaptic mitochondrial failure and synaptic degeneration.

Currently, there are no selective drug targets capable of preventing the abnormal interactions between Aβ and Drp1, and of delaying the age-dependent AD process (not only the AD process, but also other the processes of other neurological diseases, such as Huntington's, Parkinson's, and ALS). The present inventors have conducted studies, the goal of which is to develop drug molecules or molecular inhibitors capable of inhibiting or reducing abnormal interactions between Aβ and Drp1 and of protecting neurons from multiple injuries caused by Aβ and Drp1 interactions and Aβ- and Drp1-induced mitochondrial and synaptic toxicities. In these studies, the inventors identified four molecules that have demonstrated their capability to: (1) delay aging in neurons, (2) protect neurons from oxidative insults, (3) inhibit abnormal protein-protein interactions and protect neurons from mutant protein(s)-induced toxicities, and (4) enhance cell survival.

Very few molecules have been developed to prevent AD, but those that are the most promising are insoluble in water, rendering them problematic treatments due to water insolubility. As such, the present inventors developed water-soluble molecules that can reduce amyloid beta (Aβ) and Drp1 levels, and that can reduce/prevent abnormal interactions between Aβ and Drp1 in Alzheimer's disease (AD) affected neurons. The present invention targets: (1) increased production and accumulation of Aβ and increased expression of Drp1, and (2) abnormal interaction between Aβ and Drp1 induce synaptic dysfunction and mitochondrial damage, resulting dysfunction of neurons affected by AD. The therapeutic compositions and methods disclosed herein involve treating AD-affected neurons with such molecules in order to reduce Aβ and Drp1 levels, and to inhibit the interaction of Aβ and Drp1.

To achieve this objective, the inventors conducted molecular docking studies and designed 82 scaffold structures. These structures were screened for existing molecules, using molecular docking software (MOE). The inventors developed the following criteria for selecting these 82 structures for further research as inhibitors of AD progression: 1) showed optimum binding energy values and 2) were capable of identifying and dissociating the binding sites of the abnormal interactions between Aβ and Drp1. To begin, the inventors selected the best molecules of the 82, which exhibited the best optimum binding energy values and binding capabilities for these proposed in vitro and in vivo studies.

The following scaffold structures were designed to: (1) delay aging and (2) inhibit abnormal protein interactions. These designed structures screened for in silico studies using molecular docking software. Further, the inventors selected molecules that showed (1) optimum binding energy values and (2) identify and dissociate the binding sites of abnormal protein interactions—Aβ and Drp1, and phosphorylated tau and Drp1; Aβ and VDAC1 and phosphorylated tau and VDAC1 in AD neurons. A: Phosphonium cation based structures; B: Quinoline based alpha aminophosphonates; C: Napthaline based alpha aminophosphonates and D: Hexahydropyramidine carboxylates structures.

A

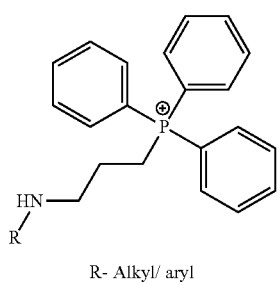

R- Alkyl/ aryl

B

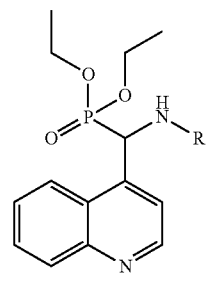

R- Alkyl/ aryl

C

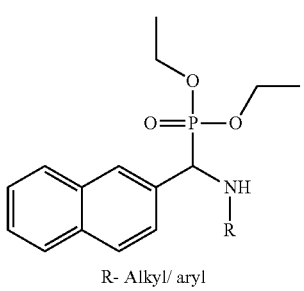

R- Alkyl/ aryl

D

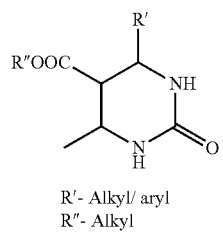

R'- Alkyl/ aryl
R"- Alkyl

Molecular Docking results. The inventors prepared a protein complex of Aβ and Drp1 by retrieving the crystal structures of Aβ (PDB ID: 1ba4) and dynamin-1-like protein (PDB ID: 4h1u) from a protein data bank. In Aβ and Drp1 complex, Ser8, Leu34, Gly120, Gly25 of Aβ are interacting with ASN98, ILU22, ASN12, Glu22 of Drp1 respectively; the inventors predicted these sites as active interacting sites of Aβ and Drp1 complex. Designed molecular structures were introduced into Aβ and Drp1 complex in order to identify the interactions of ligands in the complex and identify their inhibitory properties against Aβ-Drp1 interaction. Few molecules showed good binding score against this complex. Particularly, DDQ only interacted at specific interacting sites in the Aβ-Drp1 complex and exhibited the best docking capability and received the best docking score than all other molecules. Correspondingly, DDQ is obstructing these Aβ and Drp1 bindings by direct interactions at active sites such as ser8 and Leu34 of Aβ and ASN16 Glu16 of Drp1. DDQ is readily bound with Drp1 independently before forming a complex. Therefore, the inventors selected DDQ as a selective target to treat against AD neuronal cells. The inventors synthesized DDQ by following protocol. Table 1 is a summary of molecular docking of the Drp1 compounds.

TABLE 1

Molecular docking of the Drp1 compounds.

| Ligand | Docking Score (Kcal/mol) | Number of H-bonds | Interacting Residues |
| --- | --- | --- | --- |
| DDQ | −10.8462 | 1 | Arg225 (C=O → O—P) |
|  |  | Arene-cationic interactions | Arg225 |
| MitoQ | −9.8205 | 1 | Arg225 (C=O → HO) |
|  |  | Arene-cationic interactions | Arg225 |
| Dynasore | −9.0080 | 2 | Glu220 (C=O → HO) |
|  |  |  | Glu220 (C=O → HO) |
| Midvil | −7.0117 | 1 | Arg225 (C=O → OMe) |
|  |  | Arene-cationic interactions | Arg225 |

DDQ (diethyl(3,4-dihydroxyphenethylamine)(quinolin-4-yl)methylphosphonate):

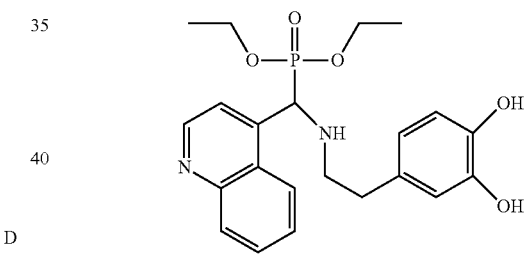

MitoQ (Phosphonium, [10-(4,5-dimethoxy-2-methyl-3,6-dioxo-1,4-cyclohexadien-1-yl)decyl]triphenyl-, methanesulfonate), in the non-limiting form of a mesylate.

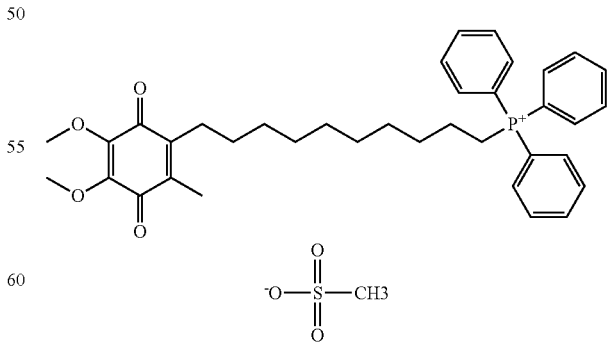

Dynasore (3-Hydroxy-naphthalene-2-carboxylic acid (3,4-dihydroxy-benzylidene)-hydrazide) in the non-limiting form of a hydrate:

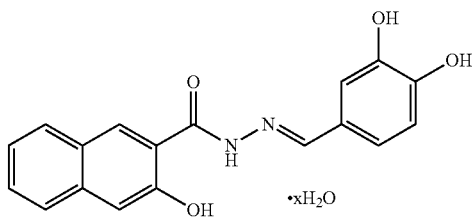 [SMILES: O=C(N/N=C/c1ccc(O)c(O)c1)c1cc2ccccc2cc1O]

Mdivi-1 (3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone):

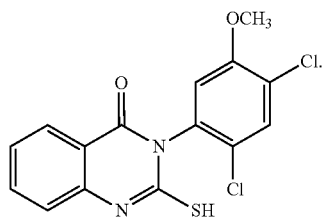 [SMILES: COc1cc(-n2c(S)nc3ccccc3c2=O)c(Cl)cc1Cl]

Each of the compounds can be formulated with one or more pharmaceutically acceptable salts, and if applicable, hydrates, solvates, tautomeric forms, stereoisomers, and prodrugs of the compounds described herein.

As used herein, the terms "pharmaceutically acceptable" or "physiologically acceptable" refer to compounds, salts, compositions, dosage forms and other materials which are useful in preparing a pharmaceutical composition that is suitable for veterinary or human pharmaceutical use.

As used herein, the term "pharmaceutically acceptable salt" of a given compound refers to salts that retain the biological effectiveness and properties of the given compound, and which are not biologically or otherwise undesirable.

As used herein, the terms "pharmaceutically acceptable salts" or "physiologically acceptable salts" refer to salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$ (substituted alkyl)), di(substituted alkyl) amines (i.e., $HN(substituted\ alkyl)_2$), tri (substituted alkyl) amines (i.e., $N(substituted\ alkyl)_3$), alkenyl amines (i.e., $NH_2$(alkenyl)), dialkenyl amines (i.e., $HN(alkenyl)_2$), dialkenyl amines (i.e., $N(alkenyl)_3$), substituted alkenyl amines (i.e., $NH_2$ (substituted alkenyl)), di(substituted alkenyl) amines (i.e., $HN(substituted\ alkenyl)_2$), tri(substituted alkenyl) amines (i.e., $N(substituted\ alkenyl)_3$, mono-, di- or tri-cycloalkyl amines (i.e., $NH_2$ (cycloalkyl), $HN(cycloalkyl)_2$, $N(cycloalkyl)_3$), mono-, di- or tri-arylamines (i.e., $NH_2$ (aryl), $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like. The term "hydrate" refers to the complex formed by the combining of a compound and water.

As used herein, the term "solvate" refers to an association or complex of one or more solvent molecules and a compound of the invention. Examples of solvents that form solvates include, but are not limited to, water, isopropanol, ethanol, methanol, dimethylsulfoxide, ethylacetate, acetic acid, and ethanolamine.

As used herein, the terms "pharmaceutically acceptable carrier" or "pharmaceutically acceptable excipient" or "excipient" refer to any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The compounds described herein, diethyl(3,4-dihydroxyphenethylamine)(quinolin-4-yl)methylphosphonate (DDQ); phosphonium, [10-(4,5-dimethoxy-2-methyl-3,6-dioxo-1,4-cyclohexadien-1-yl)decyl]triphenyl-, methanesulfonate) (MitoQ); (3-Hydroxy-naphthalene-2-carboxylic acid (3,4-dihydroxy-benzylidene)-hydrazide (Dynasore); and/or (3-(2,4-Dichloro-5-methoxyphenyl)-2,3-dihydro-2-thioxo-4 (1H)-quinazolinone, 3-(2,4-Dichloro-5-methoxyphenyl)-2-sulfanyl-4(3H)-quinazolinone) (Mdiv-1), may be modified as will be known by the skilled artisan to target those regions of the molecules shown as clouds in FIG. 1A, for example, any of these regions may be modified or substituted with one or more of the following: alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, halogen, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, hydrogen, alkyl, alkenyl, alkynyl, heteroalkyl, cycloalkyl, aryl, heteroaryl or heterocyclyl Synthesis of diethyl (3,4-dihydroxyphenethylamino)(quinolin-4-yl)methylphosphonate. Synthesis of diethyl (3,4-dihydroxyphenethylamino)(quinolin-4-yl)methylphosphonate (DDQ). To synthesize DDQ, the inventors followed two steps pudovik reaction. In the first step 4-(2-(quinolin-4-ylmethyleneamino)ethyl)benzene-1,2-diol was prepared by stirring 4-(2-aminoethyl)benzene-1,2-diol with quinoline-4-carbaldehyde at reflection temp 80° C. of THF. The inventors isolated the intermediates and 4-(2-(quinolin-4-ylmethyleneamino)ethyl)benzene-1,2-diol is selected for the second step reaction. In the second step, Dethylphosphite (DEP) was added to the solution of (Z)-4-(2-(quinolin-4-ylmethyleneamino)ethyl)benzene-1,2-diolin in drop-wise fashion, at room temperature in the presence of the $SiO_2 \cdot OSO_3H$ catalyst. The reaction mixture was stirred continuously for 4 hours at 65° C. The reaction between DEP and Z)-4-(2-(quinolin-4-ylmethyleneamino)ethyl)benzene-1,2-diol was monitored by thin-layer chromatography, using silica gel as the adsorbent and a mixture of ethyl acetate and hexane (1:2) as the eluent. After the reaction was complete, the mixture was quenched with water, and four samples of ethyl acetate (each at 10 mL) were then extracted. The samples were concentrated, using reduced pressure. The resulting mixture was purified by column chromatography, using a 100-200 mesh silica gel as the adsorbent and a mixture of ethyl acetate and hexane (1:4) as the eluent, to derive the pure DDQ.

Spectral data for diethyl (3,4-dihydroxyphenethylamino)(quinolin-4-yl)methylphosphonate (DDQ). Yield: 82%; IR (KBr): 3509 and 3472 (2OH), 3309 (N—H), 1270 (P=O), 1019 (P—C Ar) cm$^{-1}$; $^1$H NMR (400 MHz, DMSO-d6): δ 1.18 (CH$_3$, 6H), 2.61-2.92 ((Ar—CH$_2$ and CH$_2$—NH, 4H), 3.13 (NH, 1H), 4.12 (CH$_2$—CH$_3$, 4H), 4.82 (P—CH, 1H), 6.68-8.55 (9 ArH), 9.38 and 9.45 (Ar—OH, 2); $^{31}$P NMR (161.9 MHz, DMSO-d6): δ 8.935; [ref. 46] LC MS (%): m/z 431.7 (19%) [MH$^+$.], 430.9 (89%) [M$^+$.], 236.0 (100%) [ref. 47-48].

Figure 3:
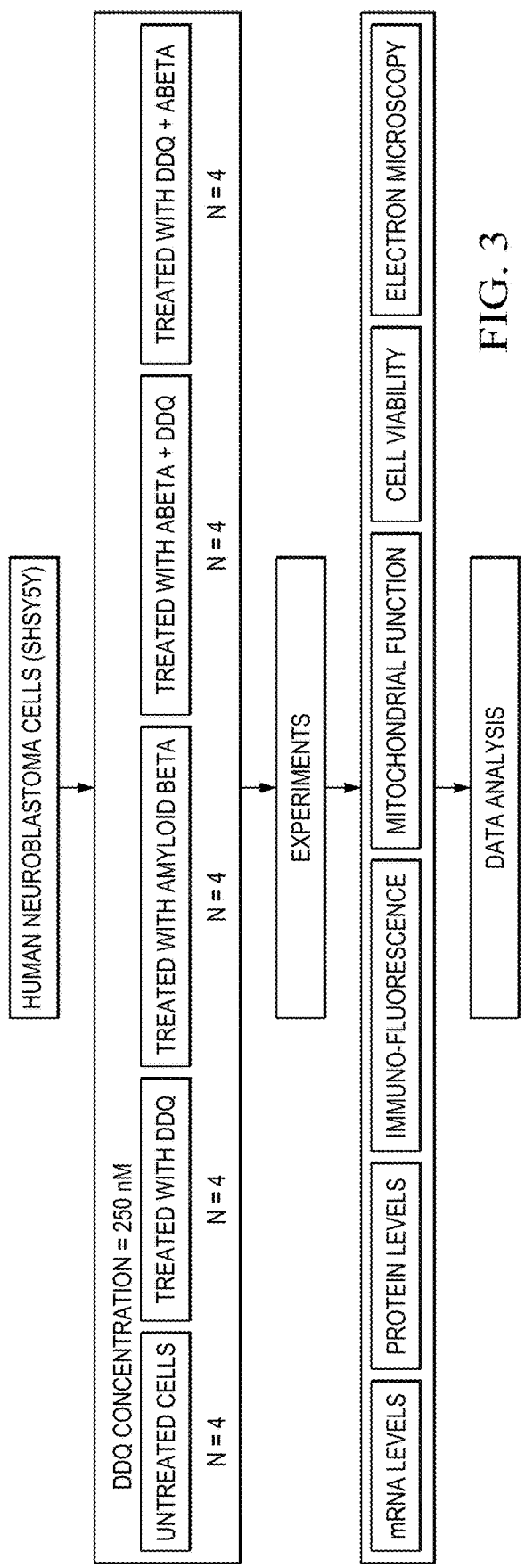
FIG. 3 is a flowchart with the strategy of DDQ treatments in cell cultures.

Based on the molecular docking results, synthesized DDQ is forwarded to screen its reducing effect of Aβ and Drp1 levels and to determine its inhibiting capacity against Aβ and Drp1 complex formation. So that, the inventors treated DDQ in human neuroblastoma (SHSY5Y) cells as shown in FIG. 3. These treated cells were used to quantify the effect of DDQ on gene expression and protein levels of synaptic, AD-related, and mitochondrial-related genes. The inventors determined the Aβ and Drp1 interaction inhibitory property of DDQ and also quantified the number of mitochondria in the treated cells.

mRNA levels of mitochondrial dynamics, mitochondrial biogenesis and synaptic genes. Using the reagent TriZol (Invitrogen), the inventors isolated total RNA from all DDQ-treated and untreated cells. mRNA levels of mitochondrial dynamic (Drp1, Fis1, Mfn1 and Mfn2), mitochondrial biogenesis genes (PGC1α, Nrf1, Nrf2 and TFAM) and synaptic genes (PSD95, synaptophysin, synapsin 1, synapsin 2, synaptobrevin 1, synaptobrevin 2, synaptopodin, and GAP43) were measured by using Sybr-Green chemistry-based quantitative real time RT-PCR.

As shown in Table 2, in Aβ treated cells Drp1 and in Fis1 (mitochondrial fission genes) expression levels were significantly increased by 2.2 fold (P=0.004), and 1.7 fold (P=0.003) respectively, compared to untreated cells. In contrast, mRNA expression levels of mitochondrial fusion genes were significantly decreased (Mfn1 by 2.3 fold (P=0.005) and Mfn2 by 2.6 fold (P=0.001)) in Aβ treated cells relative to untreated cells. This indicating the presence of abnormal mitochondrial dynamics in cells treated with Aβ. Drp1 (2.2 fold decrease, P=0.01 in DDQ treated cells) and Fis1 (4.4 fold decrease, P=0.001) mRNA levels were significantly decreased and fusion genes, Mfn1 (1.7 fold P=0.02) and Mfn2 (2.3 fold P=0.002) mRNA levels are increased in DDQ treated cells relative to untreated cells. mRNA changes were significantly reduced for fission genes Drp1 and Fis1, and increased for fusion genes Mfn1 and Mfn2 in cells incubated with Aβ and then treated with DDQ relative to untreated cells. Similarly, cells pretreated with DDQ and incubated with Aβ relative to untreated cells, mRNA levels were unchanged for fission genes Drp1 and Fis1, and fusion genes Mfn1 and Mfn2.

TABLE 2 mRNA fold changes of mitochondrial structural, mitochondrial biogenesis and synaptic genes in Human Neuroblastoma (SHSY5Y) cells treated with DDQ, Aβ, Aβ + DDQ and DDQ + Aβ relative to the untreated SHSY5Y cells and cells treated with Aβ + DDQ and DDQ + Aβ relative to the Aβ-treated SHSY5Y cells.

| Genes | mRNA fold changes compare with untreated cells | | | | mRNA fold changes compare with Aβ treated cells | |
|---|---|---|---|---|---|---|
| | DDQ | Aβ | Aβ + DDQ | DDQ + Aβ | Aβ + DDQ | DDQ + Aβ |
| Mitochondrial Structural genes | | | | | | |
| Drp1 | −2.2* | 2.2** | 1.9* | −2.1* | −1.7* | −4.6*** |
| Fis1 | −4.4*** | 1.7* | −1.2 | −1.3 | −2.0* | −2.5* |
| Mfn1 | 1.7* | −2.3** | 1.4 | 1.2 | 3.3** | 2.9** |
| Mfn2 | 2.3** | −2.6** | 1.3 | 1.1 | 3.4** | 2.9** |
| Synaptic genes | | | | | | |
| Synaptophysin | 1.4* | −3.7*** | −2.4* | −1.6* | 1.6* | 2.4* |
| PSD95 | 1.4* | −2.5** | −1.4* | −1.2 | 1.8* | 2.1* |
| Synapsin1 | 1.0 | −1.9* | 1.1 | 1.3 | 2.1* | 2.5* |
| Synapsin2 | 1.7* | −1.4* | 1.1 | 1.8* | 2.4* | 2.9** |
| Synaptobrevin1 | 1.0 | −2.4** | −1.1 | −1.4 | 2.0* | 1.7* |
| Synaptobrevin2 | 1.3 | −2.3* | 1.0 | 1.0 | 2.1* | 2.3* |
| Synaptopodin | 1.0 | −2.3** | −1.1 | −1.1 | 2.0* | 2.1* |
| GAP43 | 1.2 | −1.9** | 1.1 | 1.1 | 1.7* | 1.7* |
| Mitochondrial Biogenesis genes | | | | | | |
| PGC1a | 1.5* | −4.4** | −1.8* | −1.1 | 2.5* | 3.9** |
| Nrf1 | 1.9* | −4.1** | −1.7* | 1.1 | 2.6** | 4.9*** |

TABLE 2-continued mRNA fold changes of mitochondrial structural, mitochondrial biogenesis and synaptic genes in Human Neuroblastoma (SHSY5Y) cells treated with DDQ, Aβ, Aβ + DDQ and DDQ + Aβ relative to the untreated SHSY5Y cells and cells treated with Aβ + DDQ and DDQ + Aβ relative to the Aβ-treated SHSY5Y cells.

| Genes | mRNA fold changes compare with untreated cells | | | | mRNA fold changes compare with Aβ treated cells | |
|---|---|---|---|---|---|---|
| | DDQ | Aβ | Aβ + DDQ | DDQ + Aβ | Aβ + DDQ | DDQ + Aβ |
| Nrf2 | 2.7* | −2.8* | −1.3 | −1.1 | 2.1* | 2.6* |
| TFAM | 1.7* | −4.6*** | −2.0* | −1.5* | 2.3* | 3.2** |

Mitochondrial biogenesis genes (PGC1α, Nrf1, Nrf2 and TFAM) expressions were significantly decreased in Aβ effected neuronal cells and healthy increase in DDQ treated cells relative to untreated cells. Biogenesis genes mRNA expression of Aβ effected neuronal cells was decreased as PGC1α by 4.4 fold (P=0.001), Nrf1 by 4.1 fold (P=0.004), Nrf2 by 2.8 fold (P=0.01) and TFAM by 4.6 fold (P=0.002)) relative to untreated cells. Biogenesis genes mRNA levels in DDQ treated cells relative were significantly increased as PGC1α (1.5 fold decrease, P=0.02), Nrf1 by 1.9 fold (P=0.01), Nrf2 by 2.7 fold (P=0.01) and TFAM by 1.7 fold (P=0.02) relative to untreated cells (Table 2). These observations indicate that DDQ increases mitochondrial biogenesis activity. Mitochondrial biogenesis genes PGC1α (2.5 fold P=0.01), Nrf1 (2.6 fold P=0.003), Nrf2 (2.1 fold P=0.03) and TFAM (2.3 fold P=0.01) levels were significantly increased in cells incubated with Aβ followed by treated with DDQ relative to Aβ treated cells. DDQ pretreated followed by Aβ incubated cells exhibited increased of mRNA levels for biogenesis genes (PGC1α (3.9 fold P=0.002), Nrf1 (4.9 fold P=0.0003), Nrf2 (2.6 P=0.01) and TFAM (3.2 P=0.002)) relative to Aβ treated cells. These results suggest that DDQ pretreatment prevented Aβ induced biogenesis toxicity.

In cells treated with Aβ compared with untreated cells, mRNA expression levels were decreased for synaptophysin by 3.7 fold (P=0.0002), PSD95 by 2.5 fold (P=0.004), synapsin1 by 1.9 (P=0.02), synapsin2 by 1.4 (P=0.04), synaptobrevin1 by 2.4 (P=0.003), synaptobrevin2 by 2.3 (P=0.01), synaptopodin by 2.3 (P=0.001) and GAP43 by 1.9 (P=0.001) indicating that Aβ reduces synaptic activity. mRNA levels were significantly increased for synaptophysin by 1.4 fold (P=0.04), PSD95 by 1.4 (P=0.03), Synapsin2 by 1.7 (P=0.01), synaptobrevin2 by 1.3, and GAP43 by 1.2 fold in DDQ treated cells relative to untreated cells. These observations indicate that DDQ boosts synaptic activity in healthy cells. In cells incubated with Aβ and then treated with DDQ relative to untreated cells, mRNA levels were increased. These observations indicate that DDQ rescued synaptic activity from Aβ induced toxicity. In cells pre-treated with DDQ and incubated with Aβ relative to Aβ cells, mRNA levels were increased for synaptic mitochondrial biogenesis and mitochondrial fusion genes, indicating that DDQ enhances synaptic and mitochondrial fusion activities.

In cells incubated with Aβ and then treated with DDQ and pretreated with DDQ and incubated with Aβ relative to Aβ treated cells, the fold change of mitochondrial fission genes (Drp1 and Fis1) were down-regulated and mitochondrial fusion genes (Mfn1 and Mfn2) were significantly upregulated. Similarly, synaptic gene expression levels were upregulated in cells incubated with Aβ and then treated with DDQ and pretreated with DDQ and incubated with Aβ relative to Aβ treated cells. This indicating that DDQ is protecting synaptic genes from Aβ.

Immunoblotting analysis. To determine the effects of Aβ on mitochondrial proteins and the useful effects of DDQ at the protein level, the inventors quantified mitochondrial proteins in five independent treatments of cells with Aβ, DDQ, Aβ+DDQ and DDQ+Aβ.

Figure 4A:
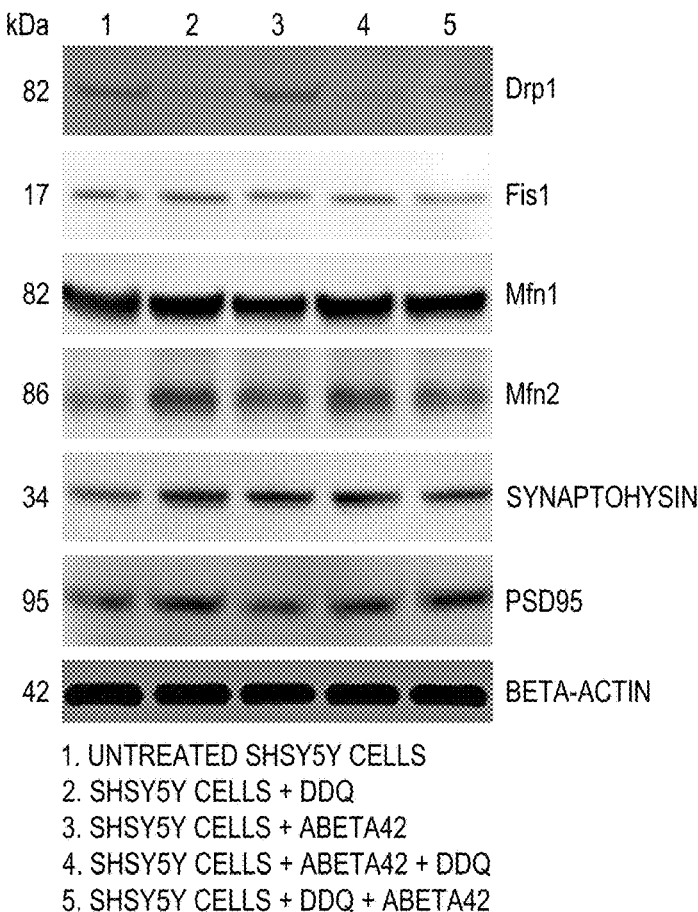
FIGS. 4A to 4C show the results of immunoblotting analysis mitochondrial dynamics, biogenesis and synaptic proteins.

Comparison with untreated cells. In SHSY5Y cells treated with Aβ compared with untreated SHSY5Y cells, significantly increased proteins levels were found for Drp1 (P=0.01) and Fis1 (P=0.01) (FIG. 4A, C). In contrast, decreased levels of mitochondrial fusion proteins, Mfn1 (P=0.002) and Mfn2 (P=0.004) were found in cells incubated with Aβ compared with untreated cells. Synaptophysin (P=0.001) and PSD95 (P=0.01) levels were significantly reduced in Aβ incubated cells relative to untreated cells (FIG. 4A, C).

Figure 4B:
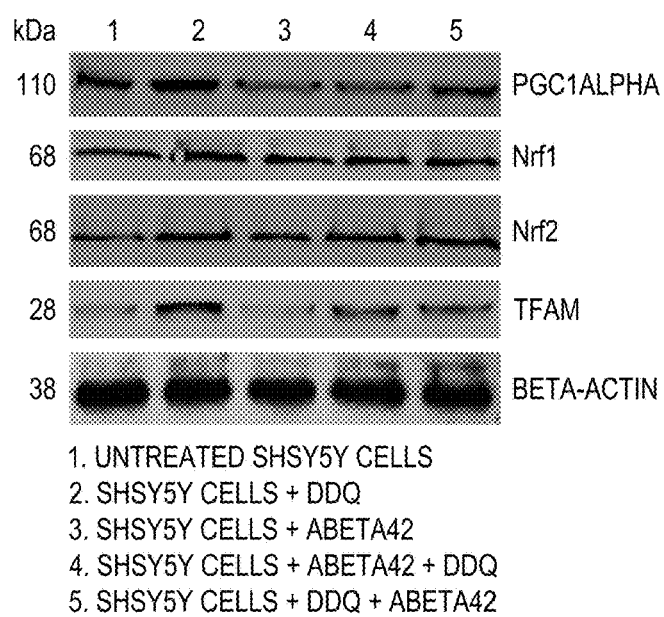

Mitochondrial fission proteins, Drp1 (P=0.03) and Fis1 were significantly reduced and fusion protein Mfn2 P=0.004 was significantly increased in DDQ treated cells relative to untreated cells (FIG. 4A, C). Mitochondrial biogenesis protein levels were significantly increased in DDQ treated cells relative to untreated cells (FIG. 4B, D).

Mitochondrial biogenesis proteins PGC1α (P=0.01), Nrf1 (P=0.001), Nrf2 (P=0.01) and TFAM (P=0.01) levels were decreased in Aβ incubated cells relative to untreated cells. Interestingly, significant increase of mitochondrial biogenesis protein levels was observed in DDQ treated cells relative to untreated cells (FIGS. 4B and D).

Mitochondrial fission proteins Drp1 (P=0.01) and Fis1 (P=0.02) were reduced and fusion protein Mfn1 (P=0.04) was significantly increased in Aβ+DDQ treated cells relative to untreated cells (FIG. 4A, C). Synaptic proteins, synaptophysin (P=0.01) and PSD95 (P=0.04) levels significantly increased in Aβ+DDQ treated cells relative to untreated cells. Decreased levels of Drp1 (P=0.004) were found in DDQ+Aβ treated cells relative to untreated cells (FIG. 4A, C). Overall, these findings suggest that DDQ reduces fission activity and enhances fusion activity in the presence of Aβ.

Figure 4C:
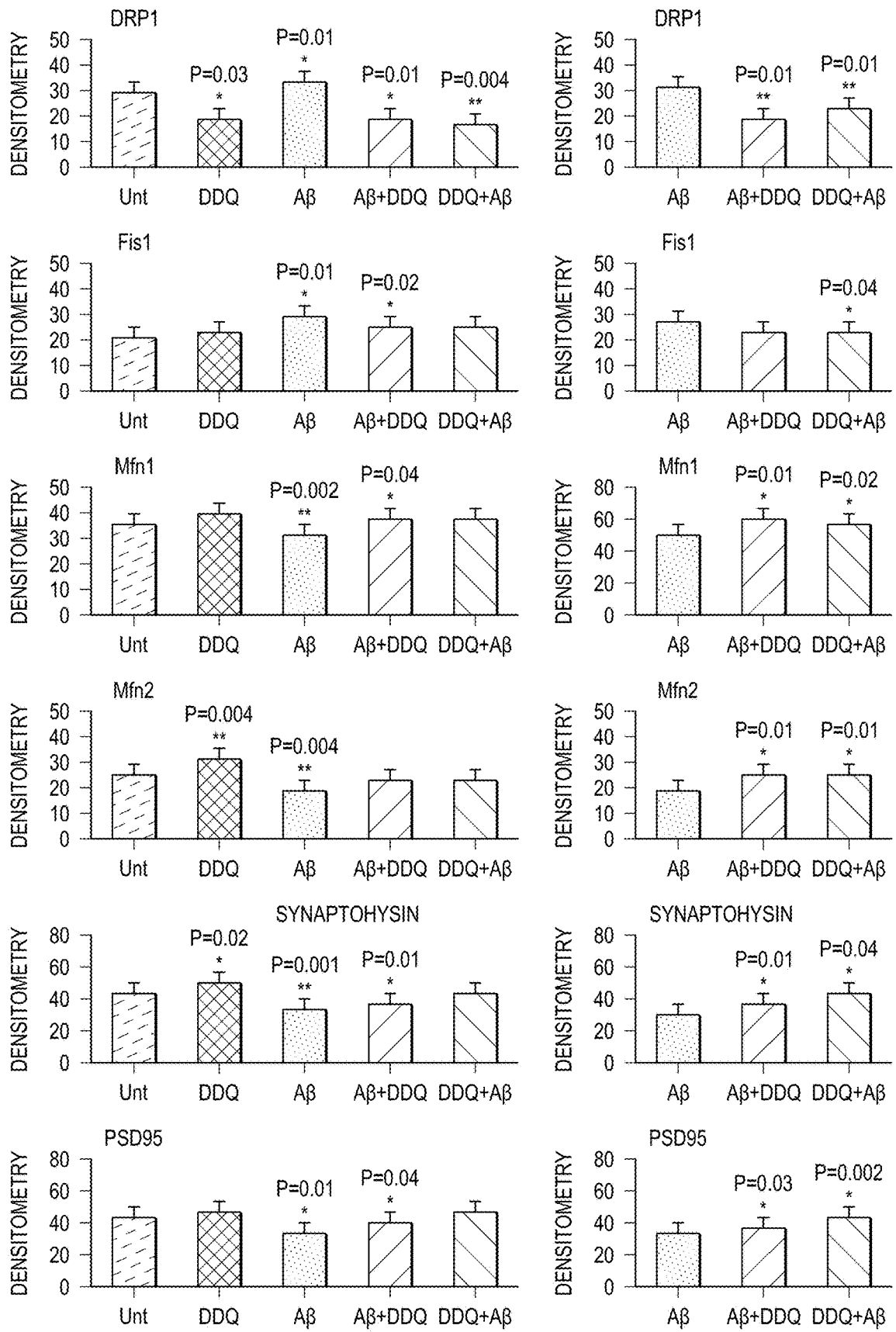

Comparison with Aβ treated cells. As shown in FIG. 4 (A, B), significantly reduced levels of fission protein, Drp1 were found in cells treated with Aβ+DDQ (Drp1, P=0.01) and DDQ+Aβ (Drp1, P=0.001; Fis1, P=0.04) relative to Aβ treated cells. In contrast, fusion proteins were increased in Aβ+DDQ (Mfn1, P=0.01; Mfn2, P=0.01) and DDQ+Aβ (Mfn1, P=0.02; Mfn2, P=0.01) treated cells relative to Aβ treated cells.

In Aβ+DDQ cells exhibited increased mitochondrial biogenesis protein levels (Nrf1 (P=0.04), Nrf2 (P=0.01) and TFAM (P=0.01) relative to Aβ treated cells. Similarly, DDQ pre-treated (DDQ+Aβ) cells showed significantly increased levels of mitochondrial biogenesis proteins (Nrf1 (P=0.01), Nrf2 (P=0.01) and TFAM (P=0.004) relative to Aβ treated cells (FIG. 4B, D).

Synaptic proteins were increased in Aβ+DDQ (synaptophysin, P=0.01; PSD95, P=0.03) and DDQ+Aβ (synaptophysin, P=0.04; PSD95, P=0.001) treated cells relative to Aβ treated cells (FIG. 4A, C), indicating that DDQ enhances synaptic activity in the presence of Aβ in cells.

Figure 5A:
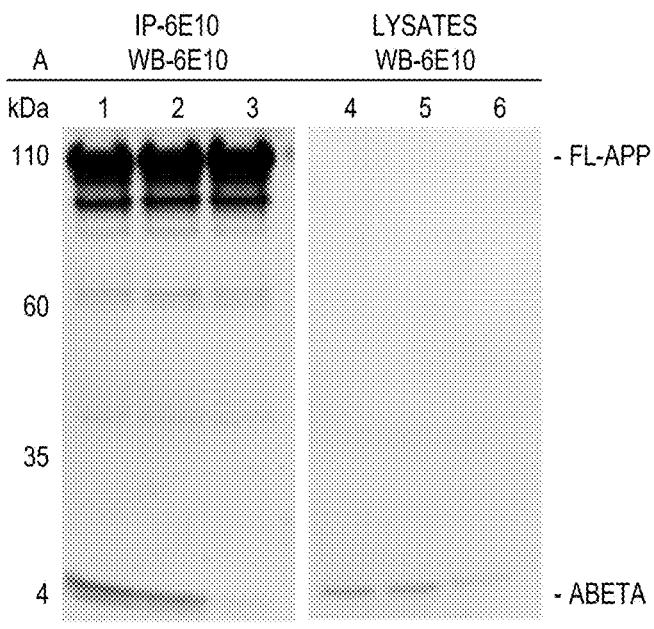
FIGS. 5A and 5B show a co-immunoprecipitation analysis of Drp1 and Aβ in SHSY5Y cells.

DDQ reduces Aβ and Drp1 levels. To determine whether DDQ reduces Aβ and Drp1 levels, the inventors conducted immunoblotting analysis, in cells treated with DDQ, Aβ+DDQ and DDQ+Aβ. As shown in FIG. 5A, the inventors found reduced levels of 4 kDa Aβ in cells treated Aβ+DDQ and DDQ+Aβ relative to cells treated with Aβ alone. The inventors also found reduced levels of Drp1 in cells treated DDQ, Aβ+DDQ and DDQ+Aβ relative to untreated and Aβ treated cells (FIG. 4A).

Figure 5B:
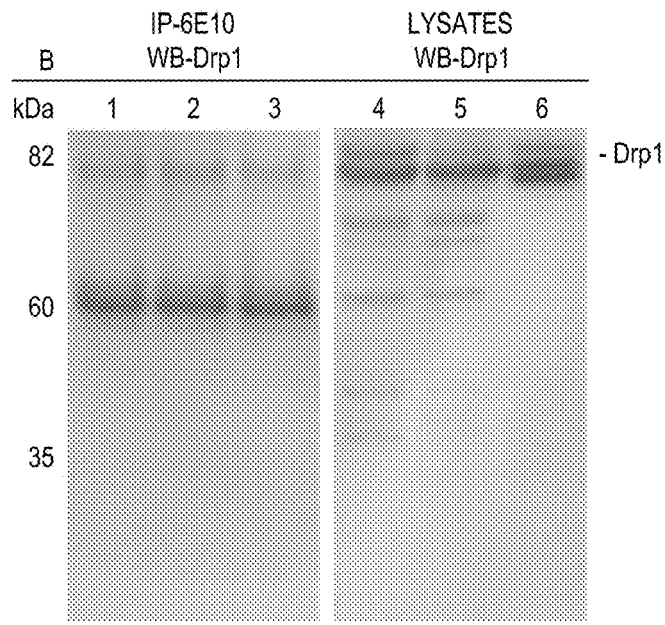

Co-immunoprecipitation and immunoblotting analysis using DDQ treated SHSY5Y cells+Aβ. To determine whether DDQ reduces the interaction of Aβ with Drp1 in Aβ incubated cells, the inventors performed co-immunoprecipitation analysis using the Drp1 antibody, and immunoblotting analysis using Aβ recognizing 6E10 antibody and protein lysates of DDQ pre-treated, DDQ post-treated and Aβ incubated cells. As shown in FIG. 5B, the inventors found reduced interaction between Aβ and Drp1 in DDQ pre-treated, DDQ post-treated relative to Aβ incubated cells. Reduced interaction was strong in DDQ pre-treated than DDQ post-treated cells, indicating that prevention is better than treatment.

Figure 6:
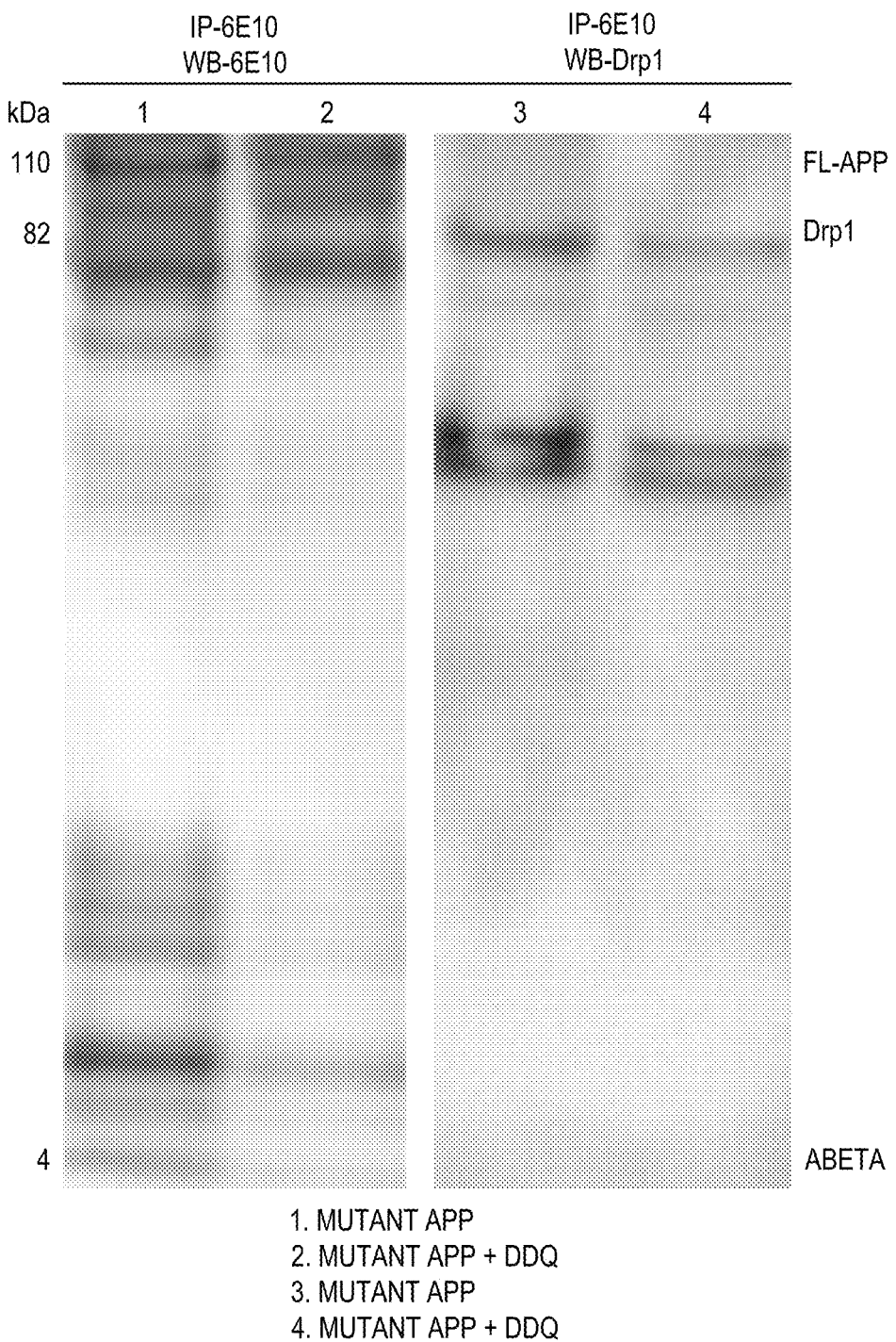
FIG. 6 shows the co-immunoprecipitation analysis of mutant APPSwe/Ind cells treated with DDQ. The inventors' transfected mutant APPSwe cDNA construct into mouse neuroblastoma (N2a) cells. After 24 hrs of transfection, cells were treated with DDQ (250 nM) for 24 hrs. Harvested mutant APPSwe/Ind cells treated and untreated with DDQ and prepared protein lysates and performed immunoprecipitation with Aβ (6E10) antibody and conducted immunoblotting analysis with 6E10 and Drp1 antibodies. Lanes 1 and 2 represents IP with 6E10 and western blot with 6E10 and lanes 3 and 4 represents IP with 6E10 and western blot with Drp1 antibody respectively. As shown in Figure, reduced levels of full-length APP and 4 kDa Aβ were found in lane 2 mutant APPSwe/Ind cells treated with DDQ compared to lane 1 of mutant APPSwe/Ind cells untreated with DDQ. Reduced levels of Drp1 were found in lane 4 of mutant APPSwe cells treated with DDQ compared to lane 3 of mutant APPSwe/Ind cells untreated with DDQ.

Co-immunoprecipitation and immunoblotting analysis of mutant $APP_{Swe/Ind}$ cells treated with DDQ. To determine whether DDQ reduces the interaction of Aβ with Drp1 in mutant $APP_{Swe/Ind}$ cells, the inventors used mutant $APP_{Swe/Ind}$ cDNA construct transfected into mouse neuroblastoma (N2a) cells and further cells were treated with DDQ. The inventors performed immunoprecipitation with Aβ (6E10) antibody and immunoblotting analysis with 6E10 and the inventors also performed co-immunoprecipitation analysis with Aβ (6E10) antibody and immunoblotting analysis with Drp1 antibody. As shown in FIG. 6, the inventors found reduced levels of full-length APP and 4 kDa Aβ in lane 2 of mutant $APP_{Swe/Ind}$ cells treated with DDQ compared to lane 1 of mutant $APP_{Swe/Ind}$ cells untreated with DDQ. The inventors also found reduced levels of Drp1 in lane 4 of mutant $APP_{Swe/Ind}$ cells treated with DDQ compared to lane 3 of mutant $APP_{Swe/Ind}$ cells untreated with DDQ. These findings further confirm that DDQ reduces full-length APP and 4 kDa Aβ and reduces interaction between Drp1 and Aβ.

Immunofluorescence analysis of Drp1, synaptophysin and PSD95. To determine the effect of Aβ and DDQ on Drp1, synaptophysin and PSD95 levels and localizations, immunofluorescence analysis was performed in cells treated as shown in FIG. 7.

Figure 7A:
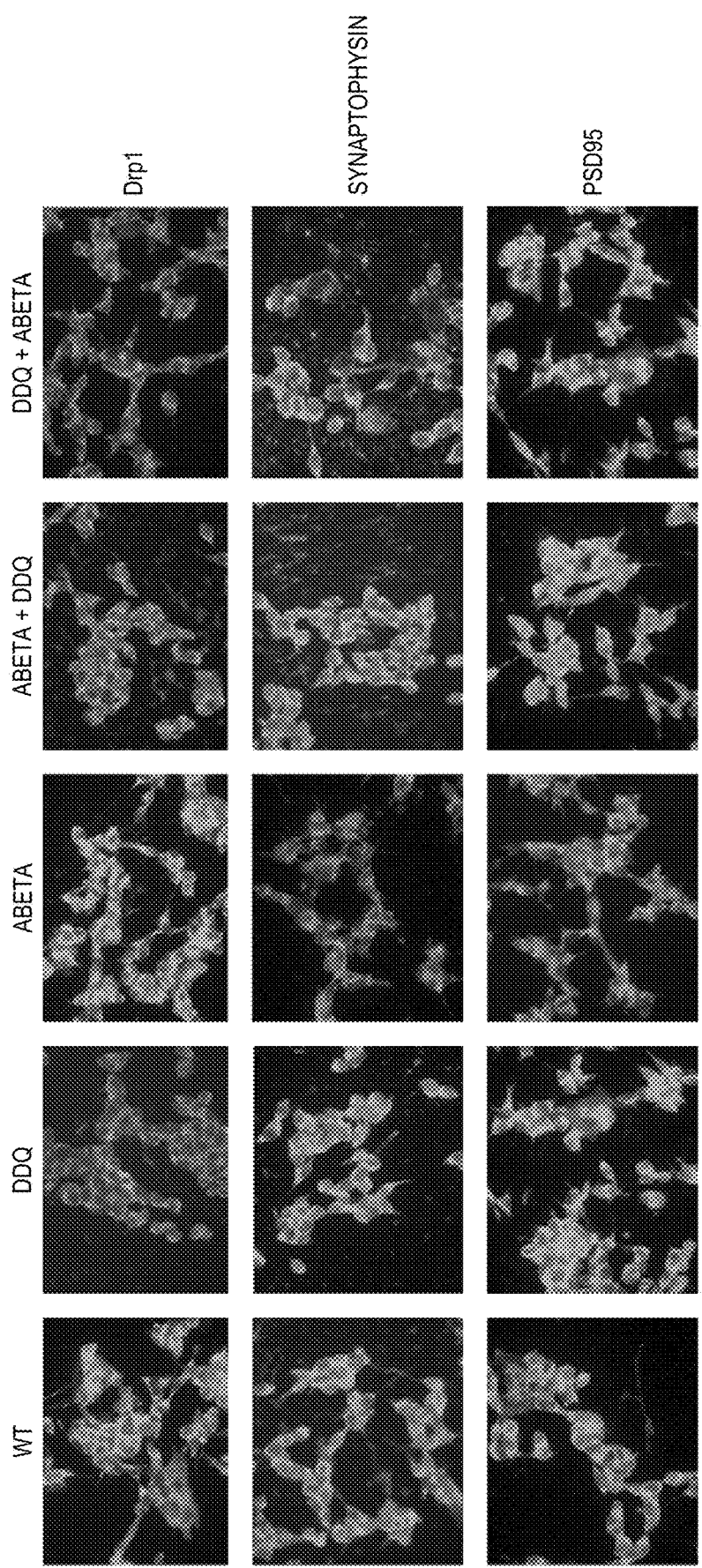
FIGS. 7A and 7B shows an immunofluorescence analysis. Immunofluorescence analysis of human neuroblastoma (SHSY5Y) cells treated with Aβ, DDQ, Aβ+DDQ and DDQ+Aβ relative to untreated cells.
Figure 7B:
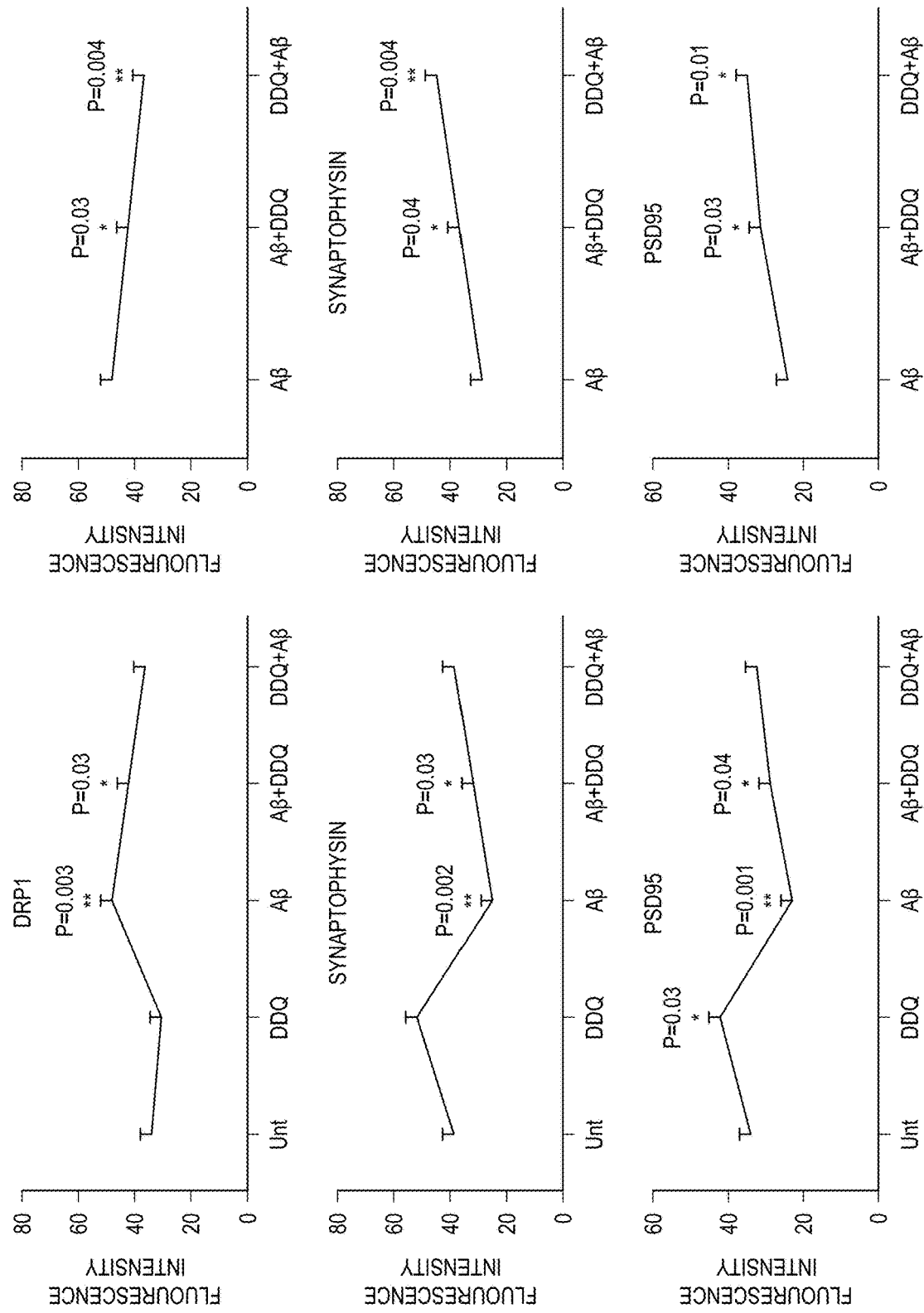

As shown in FIGS. 7A and B, the inventors found significantly increased Drp1 (P=0.003) levels in Aβ treated cells relative to untreated cells, indicating that Aβ enhances fission activity in cells. In contrast, decreased Drp1 levels were found in DDQ treated cells relative to untreated cells, but this was not significant. The synaptic proteins synaptophysin (P=0.002) and PSD95 (P=0.001) were significantly reduced in Aβ treated cells relative to untreated cells (FIGS. 7A and B).

Significantly reduced levels of fission protein Drp1 were found in cells treated with Aβ+DDQ (P=0.03) and DDQ+ (P=0.004) relative to Aβ treated cells (FIGS. 7A and B). In contrast, synaptic proteins were increased in Aβ+DDQ (synaptophysin, P=0.04; PSD95, P=0.03) and DDQ+Aβ (synaptophysin, P=0.004; PSD95, P=0.01) treated cells relative to Aβ treated cells (FIGS. 7A and B), indicating that DDQ enhances synaptic activity in the presence of Aβ in cells. Overall, the immunofluorescence findings agreed with the immunoblotting results.

Figure 8:
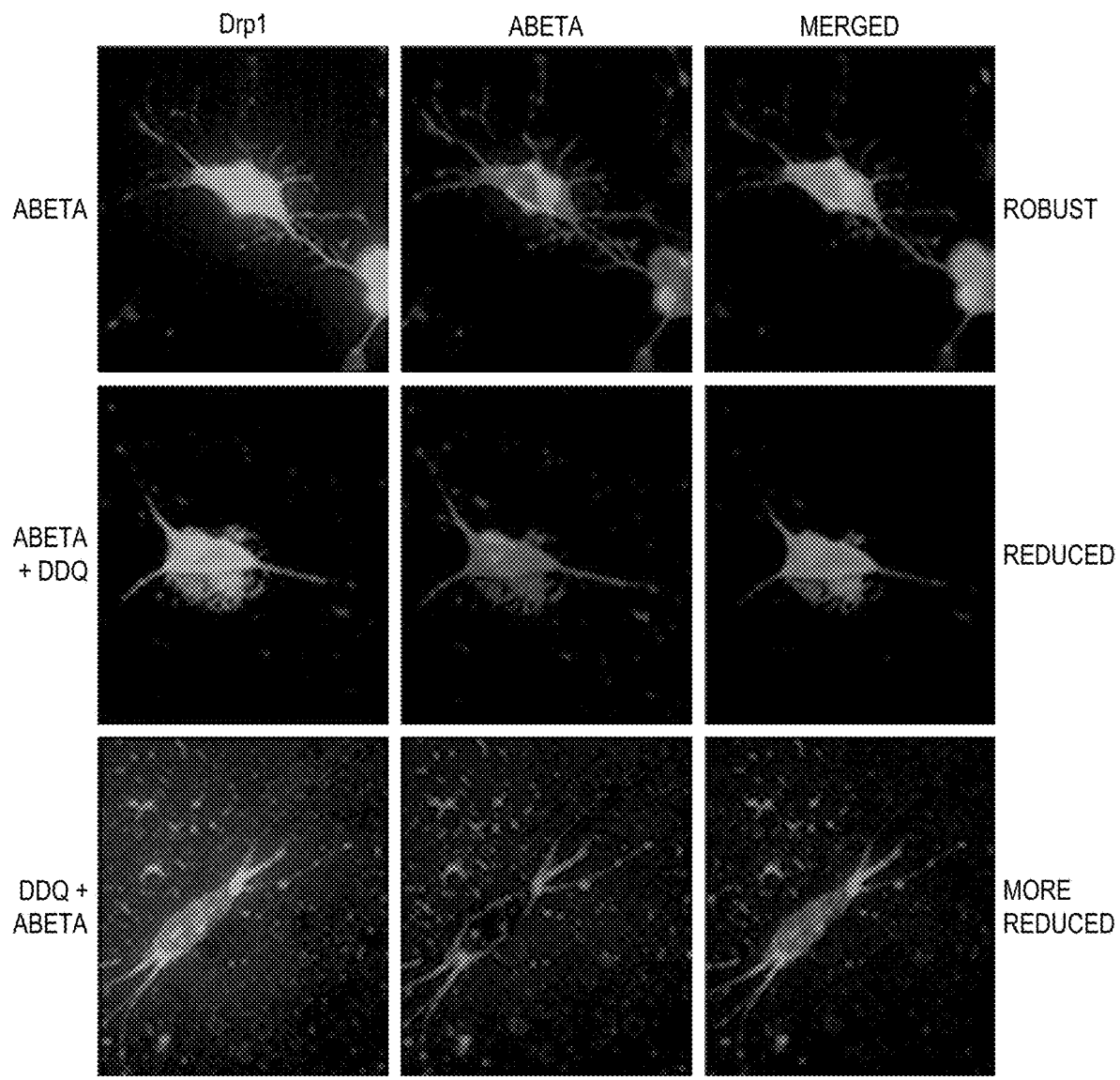
FIG. 8. Double labeling Immunofluorescence analysis of Drp1 and Aβ. Double-labeling immunofluorescence analysis of Aβ (6E10 antibody) and Drp1 in SHSY5Y cells. The localization of Drp1 (green) and Aβ (red) and the colocalization of Drp1 and Aβ (yellow, merged) at 60× the original magnification. Top panel, represents Aβ treated cells, middle panel shows Aβ+DDQ treated cells and the bottom panel shows DDQ+Aβ treated cells.

Double-labeling immunofluorescence analysis of Drp1 and Aβ. To determine whether Drp1 localizes and interacts with Aβ, the inventors conducted double-labeling analysis of Drp1 and Aβ in DDQ pre-treated, post-treated and untreated, Aβ incubated cells. As shown in FIG. 8, the immunoreactivity of Drp1 was colocalized with Aβ immunoreactivity (monomeric), indicating that Drp1 interacts with Aβ.

Further, the inventors found reduced co-localization of Drp1 with Aβ in DDQ pre-treated and post-treated Aβ incubated cells relative to Aβ incubated cells alone. Drp1 and Aβ colocalization is markedly reduced in DDQ pre-treated cells than DDQ post-treated cells. These observations matched the immunoprecipitation findings of Drp1 and 6E10. Overall, these observations suggest that DDQ reduces Drp1 and Aβ interactions.

Figure 9A:
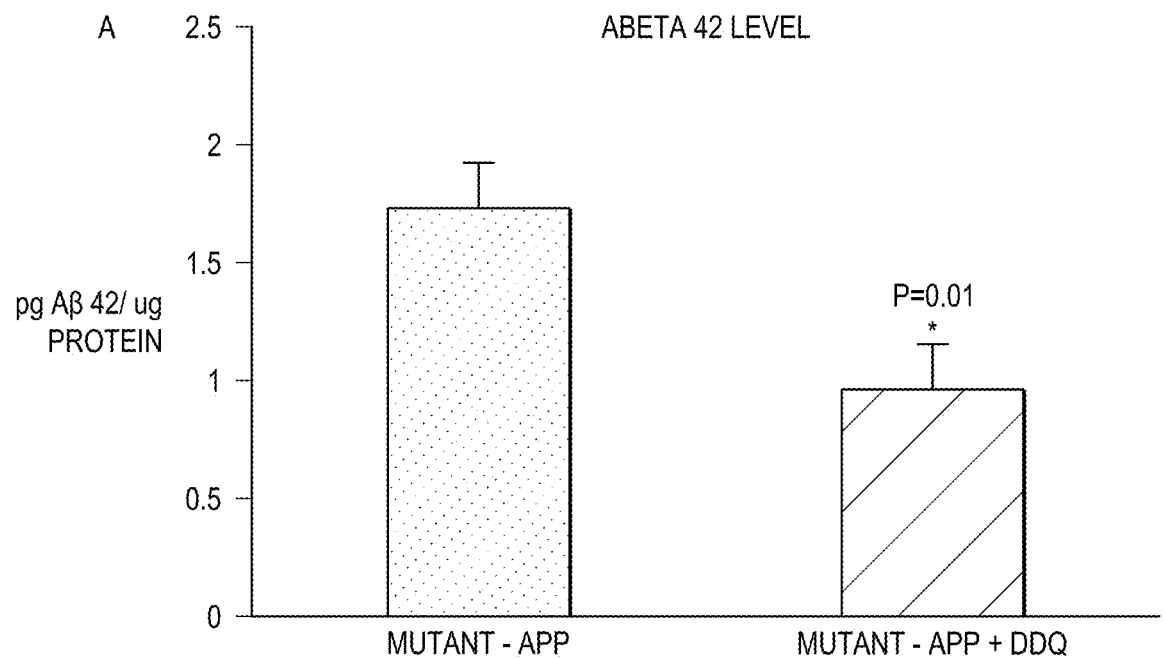
FIGS. 9A and 9B show sandwich ELISA analysis of Aβ40 and 42 in mutant APPSwe/Ind cells treated and untreated with DDQ. The inventors performed sandwich ELISA using protein lysates mutant APP cells treated and untreated with DDQ.
Figure 9B:
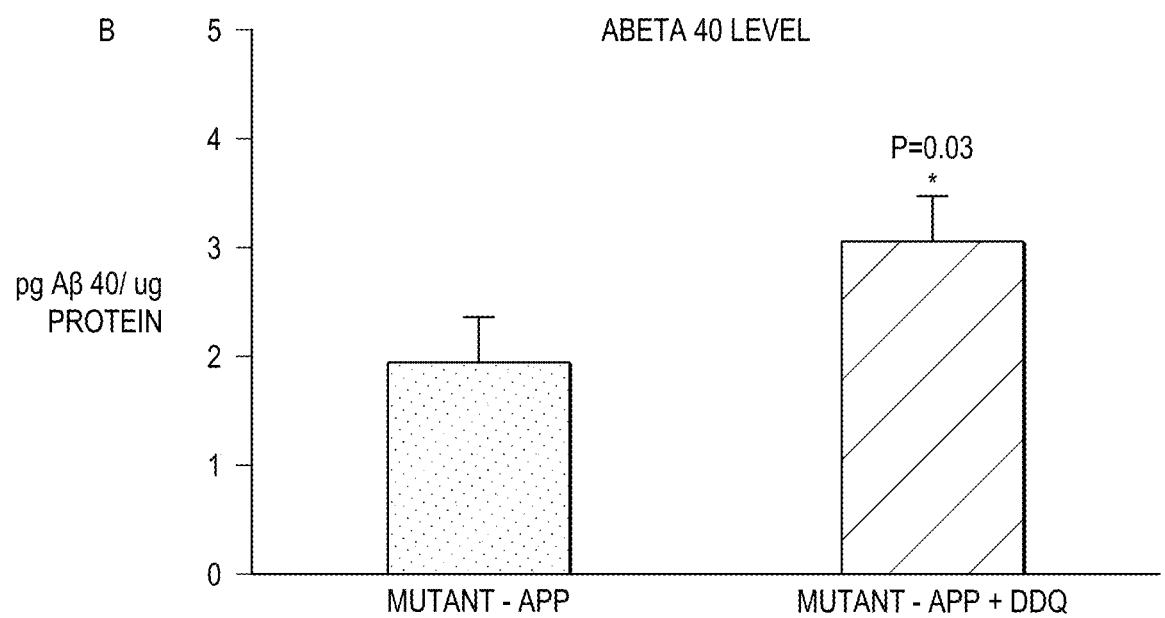

DDQ reduces soluble Aβ42 in mutant $APP_{Swe/Ind}$ cells treated with DDQ. To determine whether DDQ reduces Aβ levels, the inventors performed sandwich ELISA using protein lysates of mutant $APP_{Swe/Ind}$ cells treated with DDQ. As shown in FIG. 9, the inventors found significantly decreased levels of Aβ42 in DDQ treated mutant $APP_{Swe/Ind}$ cells (P=0.01) relative to DDQ untreated mutant $APP_{Swe/Ind}$ cells. On the contrary, Aβ40 levels were significantly increased in DDQ treated mutant $APP_{Swe/Ind}$ cells (P=0.03) relative to DDQ untreated mutant $APP_{Swe/Ind}$ cells. These observations indicate that DDQ reduces Aβ42 levels in mutant $APP_{Swe/Ind}$ cells.

Transmission electron microscopy. To determine the effects of DDQ on mitochondrial number and morphology, and any rescual effects of DDQ on mitochondria in the untreated and Aβ treated cells, the inventors used TEM on untreated, DDQ, Aβ+DDQ and DDQ+Aβ, treated SHSY5Y cells.

Figure 10:
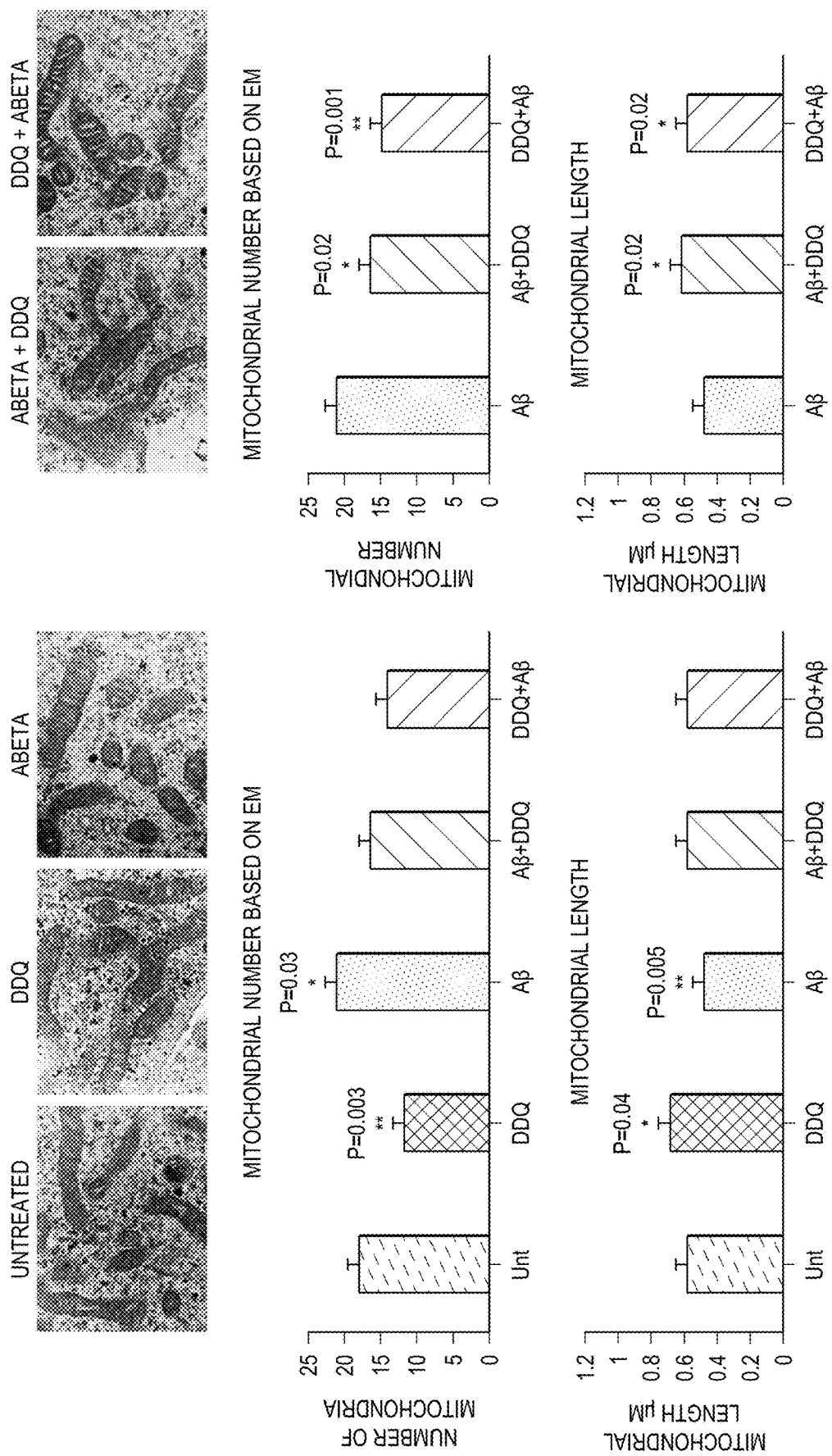
FIG. 10 shows electron microscopy of SH-SY5Y cells. The inventors quantified mitochondrial architectures within the cell in all 5 groups to identify mitochondrial number and morphology. Average number of mitochondria per cell is shown in graphs. Error bars indicate the standard deviation. Mitochondrial number is significantly decreased in DDQ-treated SH-SY5Y cells, relative to untreated cells. On the contrary, mitochondrial number is significantly increased Aβ-treated SH-SY5Y cells. DDQ-pre and post-treated cells in the presence of Aβ showed reduced mitochondrial number compared to cells treated with Aβ alone. Mitochondrial length was measured for all groups of cells. Mitochondrial length was significantly reduced Aβ-treated SH-SY5Y cells. DDQ-pre and post-treated cells in the presence of Aβ showed increased mitochondrial length compared to cells treated with Aβ alone.

Mitochondrial number and length comparison of DDQ, Aβ, Aβ+DDQ and DDQ+Aβ treated cells with untreated cells. Mitochondrial number: As shown in FIG. 10, the inventors found significantly increased number of mitochondria in Aβ treated cells relative to untreated cells (P=0.03), suggesting that Aβ treatment enhances mitochondrial number, in other words Aβ treatment enhances mitochondrial fragmentation. On the other hand, DDQ treatment reduced the number of mitochondria relative to untreated cells (P=0.003), suggesting that DDQ treatment reduces mitochondrial fragmentation. Interestingly, Aβ+DDQ and DDQ+ Aβ treated cells have exhibited approximately equal number of mitochondria relative to untreated cells (FIG. 10).

Mitochondrial length. The inventors also measured mitochondrial length in order to understand whether DDQ treatment alters mitochondrial length. As shown in FIG. 10, the inventors found mitochondrial length is significantly increased in cells treated with DDQ relative to untreated cells. On the contrary, mitochondrial length is significantly reduced in Aβ treated cells (P=0.005) relative to untreated cells. Mitochondrial length is not significantly changed in Aβ+DDQ and DDQ+Aβ treated cells relative to untreated cells, indicating that DDQ preventing/rescuing mitochondrial length in the presence of Aβ.

Mitochondrial number and length comparison of Aβ+DDQ and DDQ+Aβ treated cells with Aβ treated cells. The number of mitochondria were significantly reduced in DDQ-pre (P=0.001) and post-treated (P=0.02) cells relative to cells treated with Aβ alone (FIG. 10). Mitochondrial length is significantly increased in DDQ-pre (P=0.02) and post-treated (P=0.02) cells relative to cells treated with Aβ alone. These findings indicate that DDQ reduces excessive mitochondrial fragmentation and increased mitochondrial length in AD neurons.

Figure 11:
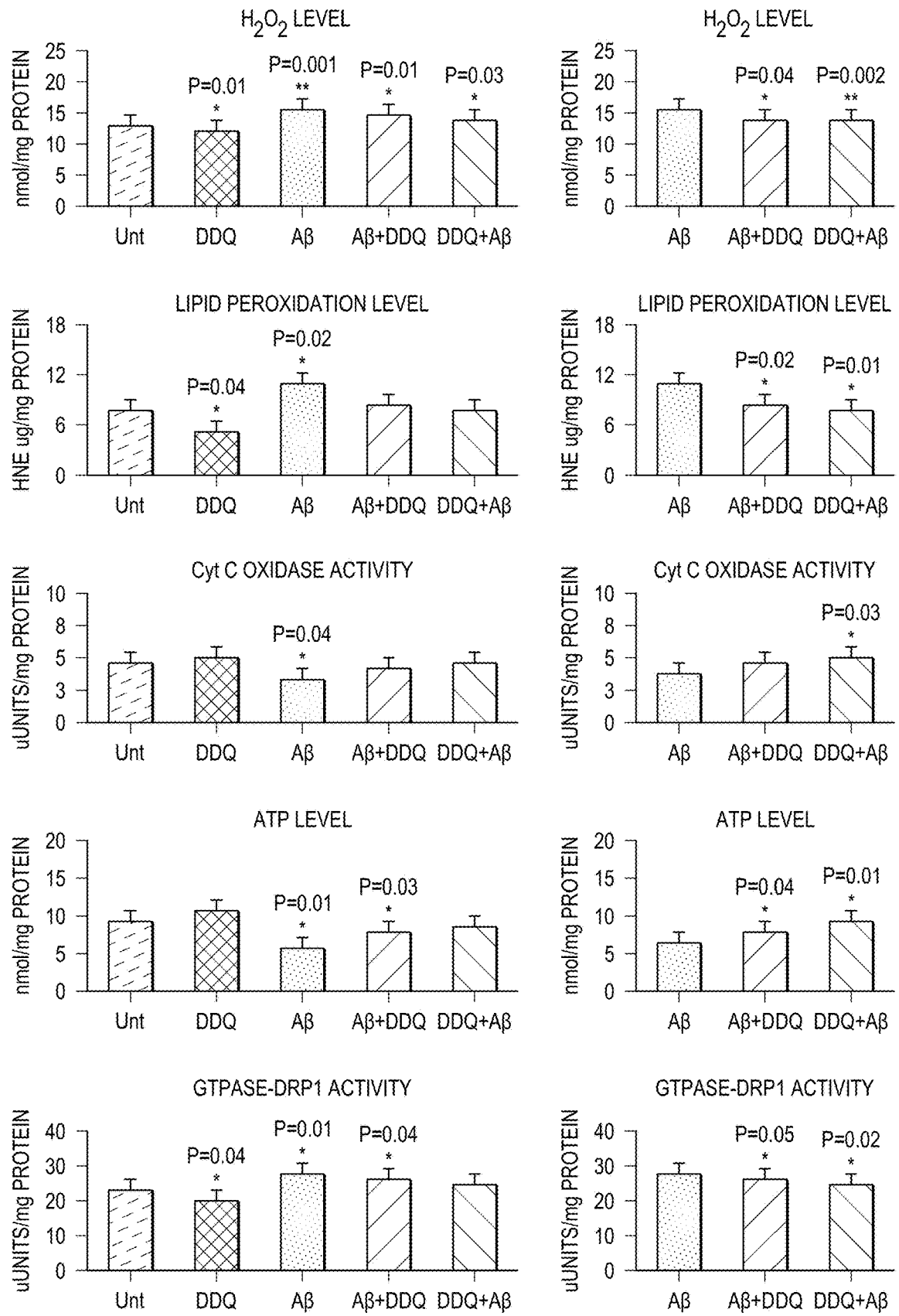
FIG. 11 shows mitochondrial function. Mitochondrial functional parameters in control human neuroblastoma (SHSY5Y) cells, in amyloid β (Aβ) incubated SHSY5Y cells, in SHSY5Y cells treated with DDQ and in SHSY5Y cells incubated with Aβ and then treated with DDQ and in SHSY5Y cells treated with DDQ and then incubated with Aβ (n=4). The inventors' analyzed mitochondrial functional data in two ways: (1) the control SHSY5Y cells were compared with the SHSY5Y cells treated with Aβ, DDQ, Aβ+DDQ and DDQ+Aβ and (2) Aβ incubated SHSY5Y cells were compared with Aβ+DDQ SHSY5Y cells and DDQ+Aβ treated cells. The inventors performed statistical analysis using ANOVA following the Dunnett correction, for: (a) H2O2 production, (b) lipid peroxidation, (c) cytochrome oxidase activity, (d) ATP levels, and (e) GTPase-Drp1 activity.

Mitochondrial functional assays. $H_2O_2$ production: As shown in FIG. 11, significantly increased levels of hydrogen peroxide ($H_2O_2$) were found in mitochondria from cells incubated with Aβ (P=0.001). In measurements taken of $H_2O_2$ from mitochondria isolated from cells treated with DDQ, significantly decreased levels of $H_2O_2$ (P=0.01) were found relative to untreated cells. These findings suggest that Aβ increases free radical production and DDQ reduces $H_2O_2$ in the presence of Aβ. Significantly increased levels were found in cells incubated with Aβ+DDQ (P=0.01) and DDQ+Aβ (P=0.03) relative to untreated cells. When the data were compared between cells incubated with Aβ and Aβ+DDQ (P=0.04) and DDQ+Aβ (P=0.002) cells, $H_2O_2$ levels were significantly reduced, indicating that DDQ reduces $H_2O_2$ levels in the presence of Aβ (FIG. 11).

Lipid peroxidation: Significantly increased levels of lipid peroxidation (4-hydroxy-nonenol) were found (P=0.002) in Aβ treated relative to untreated cells (FIG. 11). However, significantly decreased levels were found in the DDQ treated cells (P=0.04) relative to untreated cells. The inventors also found significantly reduced levels of lipid peroxidation in Aβ+DDQ (P=0.04) and DDQ+Aβ (P=0.04) relative to cells incubated with Aβ alone, indicating that DDQ reduces lipid peroxidation levels in the presence of Aβ (FIG. 11).

ATP production: As shown in FIG. 11, significantly decreased levels of ATP were found in cells that were incubated with Aβ (P=0.01) relative to untreated cells. Significantly increased levels of ATP were found in cells treated with DDQ compared with untreated cells. Significantly increased levels were found in cells incubated with Aβ+DDQ (P=0.03) relative to untreated cells (FIG. 11). Significantly increased ATP levels were found in Aβ+DDQ (P=0.04) and DDQ+Aβ treated (P=0.01) cells relative to Aβ incubated cells, indicating DDQ increases ATP levels in the presence of Aβ.

Cytochrome oxidase activity: Significantly decreased levels of cytochrome oxidase activity were found in cells that were incubated with Aβ (P=0.04) (FIG. 11). However, significantly increased levels of cytochrome oxidase activity were found in DDQ treated cells relative to untreated cells. Cytochrome oxidase activity levels were unchanged in Aβ+DDQ and DDQ+Aβ cells relative to untreated cells. Similar to ATP levels, cytochrome oxidase activity levels were increased in Aβ+DDQ and DDQ+Aβ treated (P=0.03) cells relative to Aβ incubated cells (FIG. 11), indicating DDQ increases cytochrome oxidase activity levels in the presence of Aβ.

GTPase-Drp1 activity: To determine whether Aβ affects GTPase-Drp1 activity in cells that treated with Aβ incubation, the inventors measured GTPase-Drp1 activity from Drp1 IP elutes of all cell treatments. Interestingly, the inventors also found significantly increased Drp1 enzymatic activity in Aβ treated cells (P=0.01) relative to untreated cells. The inventors found decreased levels were found in the DDQ treated cells (P=0.04) relative to untreated cells. Significantly increased Drp1 enzymatic activity was observed in cells incubated with Aβ+DDQ (P=0.04) relative to untreated cells. Drp1 enzymatic activity was reduced in cells treated like Aβ+DDQ (P=0.05) and DDQ+Aβ (P=0.02) relative to cells incubated with Aβ, indicating that DDQ reduces GTPase-Drp1 activity in the presence of Aβ (FIG. 11).

Figure 12:
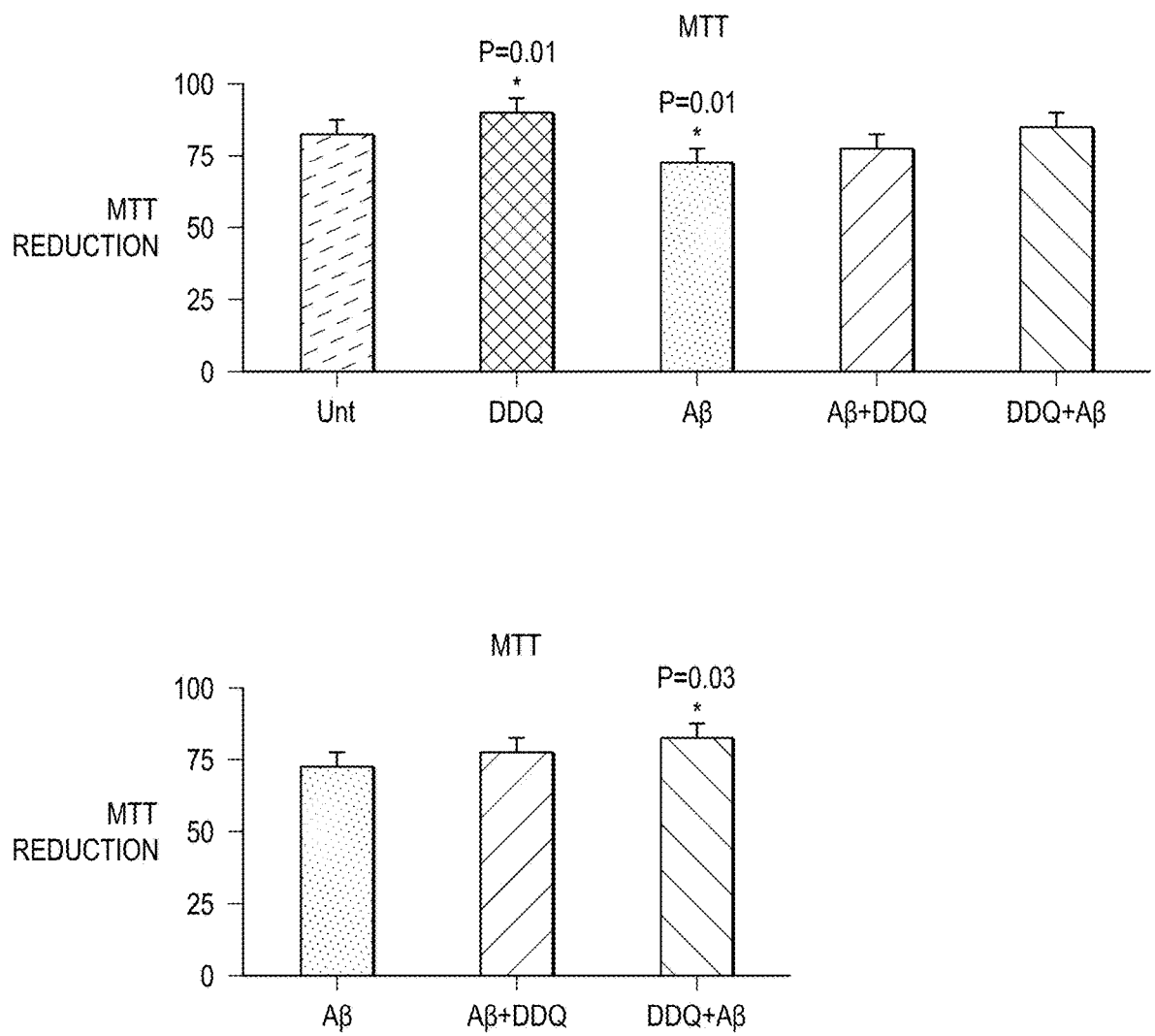
FIG. 12 shows cell viability analysis. Cell viability of human neuroblastoma (SHSY5Y) cells, while treated with DDQ, Aβ, Aβ+DDQ and DDQ+Aβ relative to untreated cells. Cell viability of pre-treated DDQ and post-treated DDQ in Aβ incubated SHSY5Y cells relative to Aβ treated cells.

Cell viability. Significantly decreased levels of cell viability were found in Aβ treated cells (P=0.01) (FIG. 12) relative to untreated cells. Cell viability was also significantly increased in cells treated with DDQ (P=0.01) compared with untreated cells. Cell viability levels were unchanged in cells treated with Aβ+DDQ and DDQ+Aβ relative to untreated cells. Significantly increased cell viability levels were found in cells treated with DDQ+Aβ (P=0.03) relative to Aβ incubated cells, suggesting that DDQ increases cell viability in the presence of Aβ.

Figure 1B:
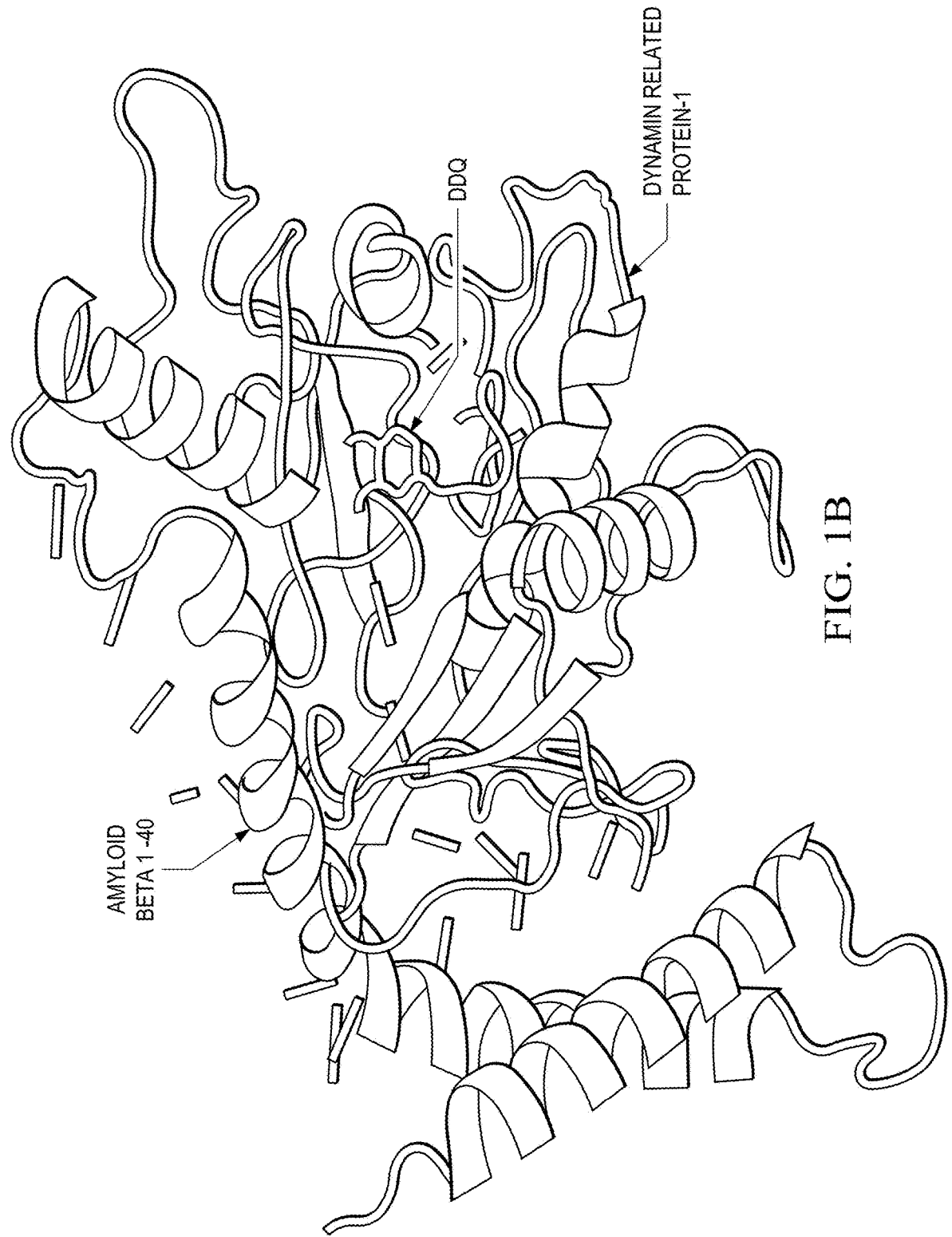
Figure 1C:
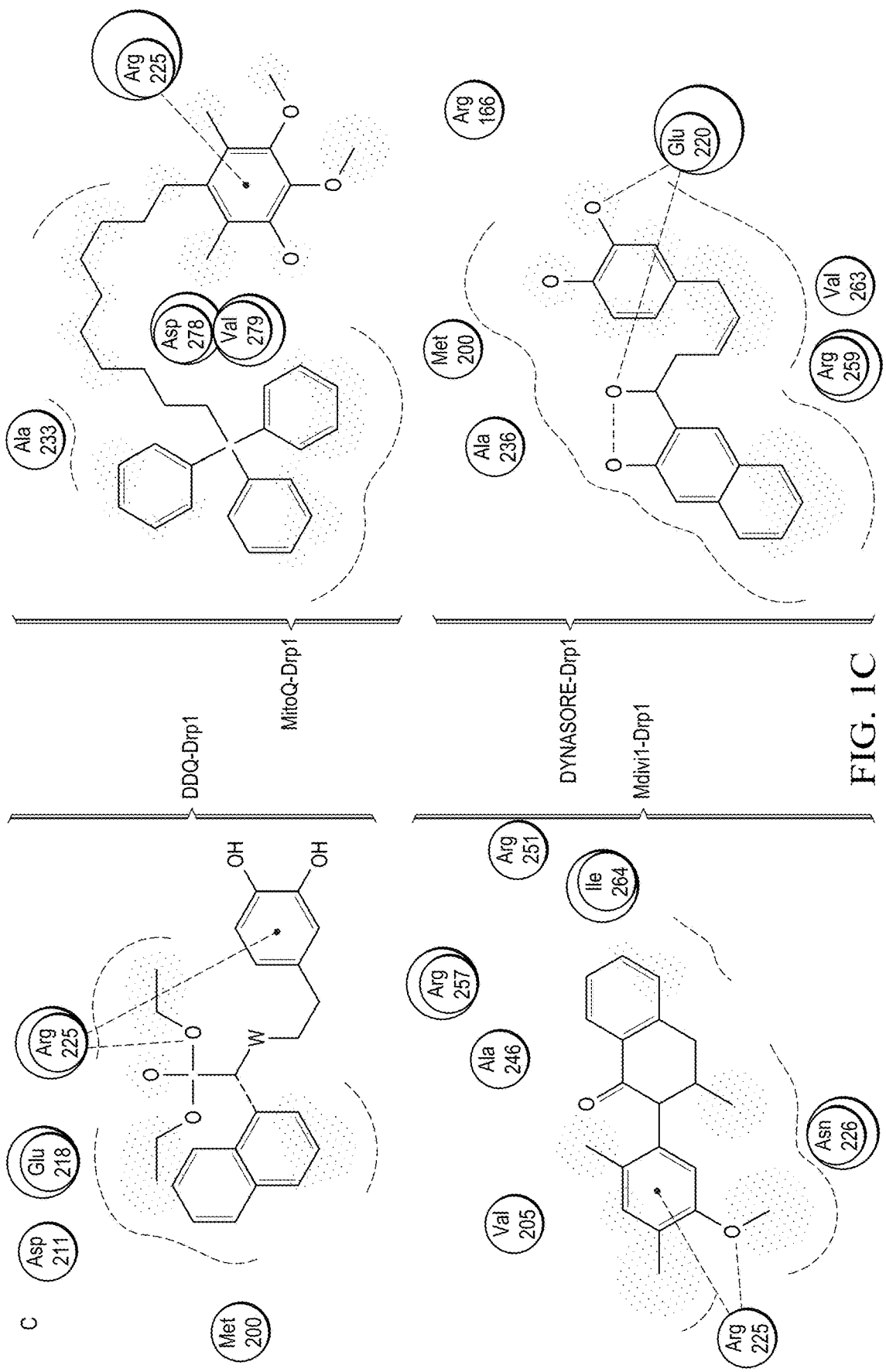
Figure 2:
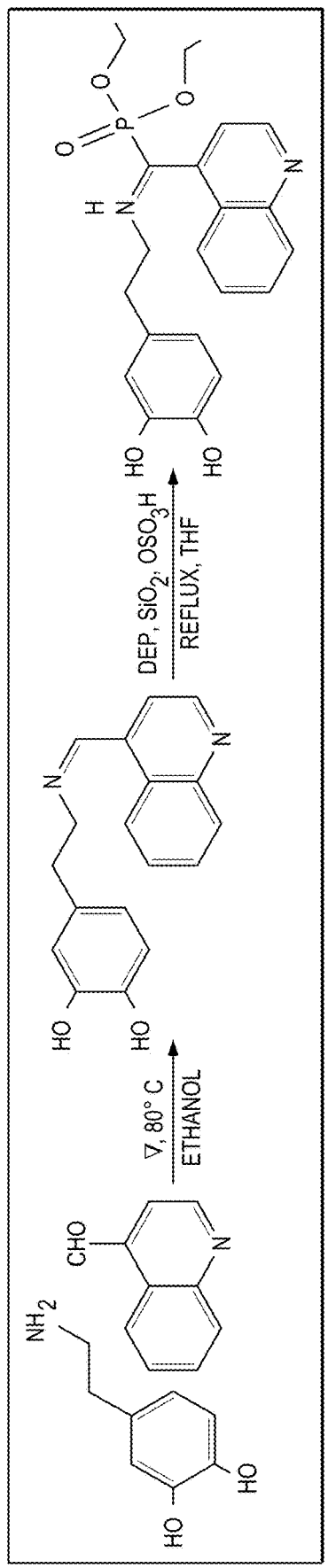
FIG. 2 shows a schematic of the synthetic procedure used to develop DDQ.

The present inventors have developed a robust and reproducible method for identifying drug molecules that reduce Drp1 and Aβ levels and also to inhibit abnormal interaction between Drp1 and Aβ that reduce excessive mitochondrial fragmentation and maintain mitochondrial function and synaptic activity in AD neurons. The elevated levels of Aβ and increased expressions of mitochondrial fission protein Drp1, and abnormal interactions between Aβ and Drp1, have been found to induce synaptic dysfunction and mitochondrial damage, causing neuronal dysfunction in AD neurons. As the target to develop aqua-soluble drug molecule, that is capable of reducing Aβ and Drp1 levels in AD neurons and also that can inhibit Aβ and Drp1 interaction, the inventors have designed 82 molecular crystal structures based on existing drug molecules and screened by molecular docking studies. The inventors designed these molecules with multiple functions including anti-inflammatory, anti-antioxidant, pro-longevity, and anti-amyloid functions. For the first time, the inventors selected DDQ as a novel drug target because, it bound at Aβ and Drp1 interacting sites to inhibit Aβ and Drp1 complex formation and also showed better docking score than other designed molecules and existing molecules such as MitoQ, Mdivi1 and SS31. Additionally, DDQ is formulated to dissolve in water. DDQ is obstructing Aβ and Drp1 binding sites by direct interactions at active sites of Aβ (ser8 and Leu34) and Drp1 (ASN16 and Glu16) (FIG. 1B). DDQ is readily bound with Drp1 (independently before forming a Drp1-Aβ complex), leaving less Drp1 binding sites with Aβ—meaning DDQ interfere with Drp1 and Aβ interactions (FIG. 1C). FIG. 2 shows a schematic of the synthetic procedure used to develop DDQ.

The inventors examined the protective effects of DDQ in healthy human neuroblastoma cells, and also in neurons incubated with Aβ42. The inventors studied preventive (DDQ+Aβ) and intervention (Aβ+DDQ) effects of DDQ against Aβ in AD neurons. The inventors measured mRNA and protein levels of mitochondrial dynamics, biogenesis and synaptic genes using real time RT-PCR, immunoblotting and immunofluorescence analysis. The inventors also assessed mitochondrial function by measuring $H_2O_2$, lipid peroxidation, cytochrome oxidase activity, GTPase-Drp1 activity and mitochondrial ATP. Further, the inventors studied cell viability using the MTT assay. Mitochondrial number and morphology was studied using transmission electron microscopy.

Mitochondrial fission protein levels were increased and fusion, biogenesis and synaptic proteins levels were decreased in Aβ treated neurons relative to untreated neurons, indicating the toxicity of Aβ. On the contrary, DDQ enhanced fusion activity; reduced fission machinery; and increased mitochondrial biogenesis & synaptic activities. DDQ pre- and post-treated of Aβ incubated cells showed appropriate mitochondrial dynamics and synaptic activities similar to untreated neurons. Likewise, DDQ pre- and post-treated of Aβ incubated neurons showed reduced abnormal mitochondrial dysfunction, maintained cell viability and synaptic activity, relative to Aβ treated neurons. Further, the protective effects of DDQ were stronger in pretreated neurons than in post-treated neurons, as such, DDQ works better in prevention than treatment in AD-like neurons. Mitochondrial count is significantly decreased in DDQ-treated neurons relative to untreated neurons. These findings strongly suggest that DDQ is a promising molecule to treat AD neurons.

DDQ reduces the levels of Aβ and Drp1 and interaction between Aβ and Drp1. Using co-immunoprecipitation, immunoblotting and double-labeling immunofluorescence analyses, the inventors studied Drp1 and Aβ and their interactions. The inventors found that Aβ interacts with Drp1 in Aβ incubated cells, and this interaction is gradually reduced by pre- and post-treatment of DDQ and the reduction of Drp1 and Aβ is stronger in DDQ pre-treated cells than post-treated. Further, the inventors also found reduced levels of Aβ and Drp1 in DDQ treated AD (Aβ+DDQ and DDQ+Aβ) neurons (FIG. 5).

Using co-immunoprecipitation and immunoblotting analysis and mutant $APP_{Swe/Ind}$ cells, the inventors also studied Drp1 and full-length APP and Aβ levels, and also Drp1 interaction with Aβ. The inventors found reduced levels of Drp1, full-length APP and Aβ in DDQ-treated mutant $APP_{Swe/Ind}$ cells relative to DDQ untreated $APP_{Swe/Ind}$ cells, indicating that DDQ reduces Drp1, full-length APP and Aβ levels in mutant $APP_{Swe/Ind}$ cells (FIG. 6).

The double-labeling immunofluorescence analysis (FIG. 8) strongly agreed with the co-IP data. The previous findings state that these interaction/colocalization increases as AD progresses (10). The double-labeling immunofluorescence analysis of Aβ and Drp1 in DDQ pre-treated and post-treated in the presence Aβ showed reduced Aβ and Drp1 colocalization relative to neurons incubated with Aβ alone.

The reduced interaction between Aβ and Drp1 may be due to the reduced synthesis/production of Aβ and Drp1 in DDQ pre- and post-treated cells. This reduced interaction of Aβ with Drp1 in DDQ pre- and post-treated cells may reduce mitochondrial fragmentation and keep mitochondria in normal count, normal length and normal function and further it may protect to neuronal cells from Aβ attack. These findings lead to the conclusion that DDQ reduced Aβ and Drp1 levels and also prevented/recused the interaction of Aβ and Drp1; and inhibit mitochondrial fragmentation in neurons affected by AD. The current findings of FIG. 5 (SHSY5Y cells pre- and post-treated DDQ and Aβ) and FIG. 6 (mutant $APP_{Swe/Ind}$ cells treated with DDQ) strongly suggest that DDQ reduces the synthesis/production of full-length APP, Aβ and Drp1 and these reduced levels of full-length APP, Aβ and Drp1 are one of the possible reasons for reduced interaction between Aβ and Drp1 in AD neurons.

Further, as expected DDQ is obstructing Aβ and Drp1 binding sites by direct interactions at active sites of Aβ (ser8 and Leu34) and Drp1 (ASN16 and Glu16) (FIG. 1). DDQ is readily bound with Drp1 (independently before forming a Drp1-Aβ complex), leaving less Drp1 binding sites with Aβ. However, additional research is needed to determine the precise effects of DDQ's role in reducing physical interaction between Aβ and Drp1.

DDQ reduces Aβ42 in mutant $APP_{Swe/Ind}$ cells. To determine whether DDQ reduces Aβ42 levels, the inventors measured both Aβ42 and Aβ40 in mutant $APP_{Swe/Ind}$ cells treated and untreated with DDQ. Interestingly, Aβ42 levels were significantly reduced and Aβ40 levels were significantly increased in DDQ-treated mutant $APP_{Swe/Ind}$ cells (FIG. 9) relative to DDQ-untreated $APP_{Swe/Ind}$ cells. These observations are interesting and may have therapeutic value for AD. It is possible that DDQ blocks/reduces the activity of epsilon cleavage site (that is responsible for Aβ42 production) at C-terminal region of Aβ in mutant $APP_{Swe/Ind}$ cells. Additional research is still needed in order to determine how DDQ reduces the levels of Aβ42 and increases Aβ40 levels in AD neurons.

DDQ maintains mitochondrial function and cell viability. To determine differences in mitochondrial function among DDQ-treated and untreated cells (as shown FIG. 3), the inventors assessed mitochondrial function assays in all treated and untreated cells. The parameters included $H_2O_2$ production, lipid peroxidation, ATP production, GTPase Drp1 enzymatic activity and cell viability. In Aβ treated cells, mitochondrial function was found to be defective and cell viability was also reduced. These observations agree with others on Aβ induced defective mitochondrial function and cell viability. Interestingly, DDQ treated cells showed enhanced mitochondrial function (FIG. 11) and increased cell viability (FIG. 12), implying that DDQ treated cells exhibited increased mitochondrial ATP, cytochrome oxidase activity and cell viability, and reduced free radicals and oxidative stress. These observations strongly suggest that DDQ reduces cellular toxicity and boosts mitochondrial function and promotes cell longevity.

In summary, for the first time, the inventors designed and synthesized DDQ based on the best docking score and its binding interactions with Aβ and Drp1 complex. In AD neurons treated with DDQ, the inventors found reduced levels of mitochondrial fission gene expressions and proteins and increased levels of mitochondrial fusion, biogenesis and synaptic gene expressions and proteins relative to neurons incubated with Aβ alone indicating that DDQ is protective against Aβ- and Drp1-induced toxicities. Hence, it is proved that DDQ have protective effects on neuronal cells and it protects against Aβ induced mitochondrial and synaptic toxicities in AD neurons. Further it is required to do more preclinical using AD mouse models and clinical studies using AD patients of DDQ to determine it's the preventive effects against Aβ induced neuronal toxicities in AD affected animal and human models.

Chemicals and Reagents: Chemicals for synthesis of DDQ were procured from Sigma-Aldrich and Merck were used as such, without further purification. All solvents used for spectroscopic and other physical studies were reagent grade and were further purified by literature methods. Infrared spectra (IR) were obtained on a Perkin-Elmer Model 281-B spectrophotometer. Samples were analyzed as potassium bromide disks. Absorptions were reported in wave numbers ($cm^{-1}$). $^1H$ and $^{31}P$ NMR spectra were recorded as solutions in DMSO-$d_6$ on a Bruker AMX 400 MHz spectrometer operating at 400 MHz for $^1H$ and 161.9 MHz for $^{31}P$ NMR. The $^1H$ chemical shifts were expressed in parts per million (ppm) with reference to tetramethylsilane (TMS) and $^{31}P$ chemical shifts to 85% $H_3PO_4$. LCMS mass spectra were recorded on a Jeol SX 102 DA/600 Mass spectrometer. Aβ 1-42 peptide was purchased from Anaspec, Fremont, Calif., USA. Dulbecco's Modified Eagle Medium/F-12 (DMEM/F12), penicillin/streptomycin, Trypsin-EDTA and fetal bovine serum were purchased from GIBCO (Gaithersberg, Md.). SHSY5Y cells. SHSY5Y cells were purchased from American Tissue Type Collection (ATCC), Virginia, USA.

Molecular docking. Molecular docking simulations were generated and prepared, using MOE software. The crystal structures of Aβ (PDB ID: 1ba4) and dynamin-1-like protein (PDB ID: 4h1u) were retrieved from the Protein Data Bank. PDB structure of Drp1 was loaded into the MOE working environment, ignoring all heteroatoms and water molecules. When receptor was loaded into MOE molecular modeling software, the heteroatoms and water molecules were removed, and polar hydrogens were added to relieve any close contact between the X and Y-axis. Protonation of the 3D structure was carried out for all of the atoms, in the implicit solvated environment at 300 K that had a pH of 7 and a salt concentration of 0.1. Electrostatic potential was applied to a cut-off value of 1.5 Å at a dielectric value of 1. A non-bonded cut-off value of 8 Å was applied to the Leonard-Jones terms. After protonation, the completed structure was energy-minimized, using the MMFF94x force field at a gradient cut off value of 0.05. Molecular dynamic simulations were carried out at a constant temperature of 300 K for a heat time of 10 picoseconds. All simulations were carried out, over a total of 2000 picoseconds. The time step was considered 0.001, and the temperature relaxation time was set to 0.2 picoseconds. The position, velocity, and acceleration were determined and the data collected and saved every 0.5 picoseconds.

PDB structure of Aβ was constructed in the MOE working environment and subjected to energy minimization. MMFF94x force fields were included, and the related potential energy terms were enabled for all bonded interactions, Van der Waals interactions, and electrostatic interactions and restraints. The non-bonded cut-off value was enabled between 8-10 Å. A generalized born implicit salvation model was enabled, all parameters were fixed, the gradient was set to 0.05, and the partial charges of the force field were enabled in order to run calculations during the minimization process. Dynamic simulations were carried out, using the Nose-Poincare-Anderson equational algorithm. Consequently, the inventors formed Aβ and Drp1 complex, which further used as receptor to find the binding interactions designed molecules.

The 3D structures of all designed structures were constructed in the MOE working environment and subjected to energy minimization. MMFF94x force fields were included, and the related potential energy terms were enabled for all bonded interactions, Van der Waals interactions, and electrostatic interactions and restraints. The non-bonded cut-off value was enabled between 8-10 Å. A generalized Born implicit salvation model was enabled, all parameters were fixed, the gradient was set to 0.05, and the partial charges of the force field were enabled in order to run calculations during the minimization process. Dynamic simulations were carried out, using the Nose-Poincare-Anderson equational algorithm. The temperature for the proteins was set to 30 K and was increased to 300 K for run-time temperature. Heat time and cool time were set to 0 picoseconds. The site for the Prediction of Binding Site for Ligand Activity of the crystallographic structure of Drp1 was defined. The MOE dock module was used to dock the compounds into specified binding sites along with the reference compound exemestane. Exemestane was found in contact with 3S7S, determined by alpha PMI (Principle Moments of Inertia) placement methodology, where Poses were generated by aligning principal moments of inertia and ligand conformations to a randomly generated subset of alpha spheres in the receptor site. Thirty docked conformations were generated for each ligand and ranked by an alpha HB scoring function, which is a linear combination of the geometric fit of the ligand to the binding site and hydrogen bonding effects. From all the receptor-ligand complexes, the conformation with the lowest docking score was chosen for additional analysis.

In vitro biological studies of DDQ. DDQ exhibited a good molecular docking score and better binding interactions compared to the other molecules those the inventors developed. Therefore, the inventors decided to quantify the biological effects of DDQ in AD pathogenesis. Therefore, the inventors treated AD neurons with DDQ and quantified the effect of DDQ on gene expression levels of synaptic, AD-related, and mitochondrial-related genes. For these treatments, the inventors performed the following protocols: The inventors treated SHSY5Y cells in five different groups as explained in FIG. 3.

FIG. 3 illustrates the experimental strategy of the cell culture work and including treatments. The cells were grown in a medium (1:1 DMEM and F12, 10% FBS, 1x penicillin, and streptomycin) at 37° C. in a humified incubator with a 5% $CO_2$ environment. After seeding were allowed to grow for 24-48 hrs or until 80% confluence in six-well plates and used for experiments. The inventors used five different groups of cells—(1) untreated SHSY5Y cells; (2) SHSY5Y cells treated with DDQ (250 nM final concentration) for 24 hrs; (3) SHSY5Y cells incubated with Aβ peptide 1-42 (20 uM final concentration) for 6 hrs; (4) SHSY5Y cells treated Aβ for 6 hrs+DDQ for 24 hrs and (5) SHSY5Y cells treated DDQ for 24 hrs and Aβ for 6 hrs. Half a million SHSY5Y cells were suspended per well into six-well plates. The inventors used Aβ peptide 1-42 and DDQ 250 nM in the experiments. After treatments, the inventors harvested cells, conducted experiments to measure the levels mRNA using Sybr-Green based real-time RT-PCR, proteins using immunoblotting and immunofluorescence analysis and cell viability using MTT assay. The inventors counted the number of mitochondria by electron microscopy.

Data were compared two ways—(1) untreated cells versus cells treated with Aβ, DDQ, DDQ+Aβ and Aβ+DDQ, and (2) Cells treated with Aβ versus DDQ+Aβ and Aβ+DDQ Quantification of mitochondrial dynamics, biogenesis and synaptic genes expression using real-time RT-PCR. Using the reagent TriZol (Invitrogen), the inventors isolated total RNA from control and experimental groups (FIG. 3). Using primer express Software (Applied Biosystems), the inventors designed the oligonucleotide primers for the housekeeping genes β-actin, mitochondrial structural genes; fission (Drp1 and Fis1); fusion genes (MFN1, MFN2); mitochondrial biogenesis genes PGC1a, Nrf1, Nrf2 and TFAM; and synaptic genes (PSD95, synaptophysin, synapsin 1, synapsin 2, synaptobrevin 1, synaptobrevin 2, synaptopodin, and GAP43). The primer sequences and amplicon sizes are listed in Table 3. Using SYBR-Green chemistry-based quantitative real-time RT-PCR, the inventors measured mRNA expression of the genes mentioned above as described by Manczak et al. [10].

TABLE 3

Summary of real-time RT-PCR oligonucleotide primers used in measuring mRNA expression in mitochondrial and synaptic genes in untreated-SHSY5Y, DDQ-SHSY5Y, Aβ-SHSY5Y, Aβ + DDQ-SHSY5Y and DDQ + Aβ-SHSY5Y treated cell line.

| Gene | DNA Sequence (5'-3') | PCR Product Size | SEQ ID NO: |
|---|---|---|---|
| Mitochondrial Structural Genes | | | |
| Drp1 | Forward Primer TGGGCGCCGACATCA | 54 | 1 |
|  | Reverse Primer GCTCTGCGTTCCCACTACGA |  | 2 |

TABLE 3-continued

Summary of real-time RT-PCR oligonucleotide primers used in measuring mRNA expression in mitochondrial and synaptic genes in untreated-SHSY5Y, DDQ-SHSY5Y, Aβ-SHSY5Y, Aβ + DDQ-SHSY5Y and DDQ + Aβ-SHSY5Y treated cell line.

| Gene | DNA Sequence (5'-3') | PCR Product Size | SEQ ID NO: |
|---|---|---|---|
| Fis1 | Forward Primer TACGTCCGCGGGTTGCT | 54 | 3 |
|  | Reverse Primer CCAGTTCCTTGGCCTGGTT |  | 4 |
| MFN1 | Forward Primer TCTCCAAGCCCAACATCTTCA | 62 | 5 |
|  | Reverse Primer ACTCCGGCTCCGAAGCA |  | 6 |
| MFN2 | Forward Primer TGGTGAGGTGCTATCTCGGA | 72 | 7 |
|  | Reverse Primer AACAGAGCTCTTCCCACTGC |  | 8 |

Synaptic genes

| Gene | DNA Sequence (5'-3') | PCR Product Size | SEQ ID NO: |
|---|---|---|---|
| Synaptophysin | Forward Primer CATTCAGGCTGCACCAAGTG | 59 | 9 |
|  | Reverse Primer TGGTAGTGCCCCCTTTAACG |  | 10 |
| PSD95 | Forward Primer GGACATTCAGGCGCACAAG | 58 | 11 |
|  | Reverse Primer TCCCGTAGAGGTGGCTGTTG |  | 12 |
| Synapsin 1 | Forward Primer TGAGGACATCAGTGTCGGGTAA | 64 | 13 |
|  | Reverse Primer GGCAATCTGCTCAAGCATAGC |  | 14 |
| Synapsin 2 | Forward Primer TCCCACTCATTGAGCAGACATACT | 63 | 15 |
|  | Reverse Primer GGGAACGTAGGAAGCGTAAGC |  | 16 |
| Synaptobrevin 1 | Forward Primer TGCTGCCAAGCTAAAAGGAA | 68 | 17 |
|  | Reverse Primer CAGATAGCTCCCAGCATGATCA |  | 18 |
| Synaptobrevin 2 | Forward Primer CGGAAGAGTCAGTCTCCATTGG | 64 | 19 |
|  | Reverse Primer CACCTGCAGATAATGTCGTGCTA |  | 20 |
| Neurogranin | Forward Primer AGCCGGACGACGACATTCTA | 79 | 21 |
|  | Reverse Primer AAACTCGCCTGGATTTTGGC |  | 22 |
| GAP43 | Forward Primer CTGAGGAGGAGAAAGACGCTGTA | 57 | 23 |
|  | Reverse Primer TCCTGTCGGCACTTTCC |  | 24 |
| Synaptopodin | Forward Primer TCCTGCGCCCTGAACCTA | 70 | 25 |
|  | Reverse Primer GACGGGCGACAGAGCATAGA |  | 26 |
| GAPDH | Forward Primer TTCCCGTTCAGCTCTGGG | 59 | 27 |
|  | Reverse Primer CCCTGCATCCACTGGTGC |  | 28 |

Mitochondrial Biogenesis genes

| Gene | DNA Sequence (5'-3') | PCR Product Size | SEQ ID NO: |
|---|---|---|---|
| PGC1α | Forward Primer GCAGTCGCAACATGCTCAAG | 83 | 29 |
|  | Reverse Primer GGGAACCCTTGGGGTCATTT |  | 30 |
| Nrf1 | Forward Primer AGAAACGGAAACGGCCTCAT | 96 | 31 |
|  | Reverse primer CATCCAACGTGGCTCTGAGT |  | 32 |
| Nrf2 | Forward Primer ATGGAGCAAGTTTGGCAGGA | 96 | 33 |
|  | Reverse Primer GCTGGGAACAGCGGTAGTAT |  | 34 |
| TFAM | Forward Primer TCCACAGAACAGCTACCCAA | 84 | 35 |
|  | Reverse Primer CCACAGGGCTGCAATTTTCC |  | 36 |

Housekeeping Genes

| Gene | DNA Sequence (5'-3') | PCR Product Size | SEQ ID NO: |
|---|---|---|---|
| Beta Actin | Forward Primer AGACCTGTACGCCAACACAG | 72 | 37 |
|  | Reverse Primer TCTGCATCCTGTCGGCAAT |  | 38 |

Immunoblotting analysis. To determine whether DDQ, or Aβ alters the protein levels of mitochondrial and synaptic genes that showed altered mRNA expressions in the real-time RT-PCR, the inventors performed immunoblotting analyses of protein lysates from cells of control and experimental treatments in independent cells treatments (n=3) as described in Manczak et al. [13]. Details of proteins, dilutions of antibodies used for immunoblotting analysis was given in Table 4.

TABLE 4

Summary of antibody dilutions and conditions used in the immunoblotting analysis of mitochondrial structural and synaptic proteins in the SHSY5Y cell treated with DDQ, Aβ, Aβ + DDQ and DDQ + Aβ.

| Marker | Primary antibody—species and dilution | Purchased from Company, State | Secondary antibody, dilution | Purchased from Company, City & State |
|---|---|---|---|---|
| Drp1 | Rabbit Polyclonal 1:500 | Novus Biological, Littleton, CO | Donkey anti-rabbit HRP 1:10,000 | GE Healthcare Amersham, Piscataway, NJ |
| Fis1 | Rabbit Polyclonal 1:500 | MBL International Corporation Woburn, Ma | Donkey anti-rabbit HRP 1:10,000 | GE Healthcare Amersham, Piscataway, NJ |
| Mfn1 | Rabbit Polyclonal 1:400 | Novus Biological, Littleton, CO | Donkey anti-rabbit HRP 1:10,000 | GE Healthcare Amersham, Piscataway, NJ - |
| Mfn2 | Rabbit Polyclonal 1:400 | Novus Biological, Littleton, CO | Donkey anti-rabbit HRP 1:10,000 | GE Healthcare Amersham, Piscataway, NJ |

TABLE 4-continued

Summary of antibody dilutions and conditions used in the immunoblotting analysis of mitochondrial structural and synaptic proteins in the SHSY5Y cell treated with DDQ, Aβ, Aβ + DDQ and DDQ + Aβ.

| Marker | Primary antibody—species and dilution | Purchased from Company, State | Secondary antibody, dilution | Purchased from Company, City & State |
|---|---|---|---|---|
| SYN | Rabbit Monoclonal 1:400 | Rabbit Monoclonal 1:400 | Donkey anti-rabbit HRP 1:10,000 | GE Healthcare Amersham, Piscataway, NJ |
| PSD95 | Rabbit Monoclonal 1:300 | Abcam, Cambridge, MA | Donkey anti-rabbit HRP 1:10,000 | GE Healthcare Amersham, Piscataway, NJ |
| PGC1α | Rabbit Polyclonal 1:500 | Novus Biological, Littleton, CO | Donkey Anti-rabbit HRP 1:10,000 | GE Healthcare Amersham, Piscataway, NJ |
| Nrf1 | Mouse Monoclonal 1:30 | Abcam, Cambridge, MA | Sheep anti-mouse HRP 1:10,000 | GE Healthcare Amersham, Piscataway, NJ |
| Nrf2 | Rabbit Polyclonal 1:300 | Novus Biological, Littleton, CO | Donkey Anti-rabbit HRP 1:10,000 | GE Healthcare Amersham, Piscataway, NJ |
| TFAM | Rabbit Polyclonal 1:30 | Novus Biological, Littleton, CO | Donkey Anti-rabbit HRP 1:10,000 | GE Healthcare Amersham, Piscataway, NJ |
| B-actin | Mouse Monoclonal 1:500 | Sigma-Aldrich, St Luis, MO | Sheep anti-mouse HRP 1:10,000 | GE Healthcare Amersham, Piscataway, NJ |

SHSY5Y cells, mutant APP$_{Swe/Ind}$ cells and co-immunoprecipitation analysis. SHSY5Y cells: To determine whether Aβ interact with Drp1, the inventors used protein lysates from Aβ incubated (DDQ pre-treated, post-treated and untreated) SHSY5Y cells.

Mutant APP$_{Swe/Ind}$ cells: The inventors purchased mutant APP$_{Swe}$ cDNA clone (pCAX-APP$_{Swe/Ind}$) from Addgene—https://www.addgene.org and verified expression of mutant APP APP$_{Swe/Ind}$ cDNA and further sub-cloned into a mammalian expression vector (Arubala P. Reddy—unpublished observations). The inventors transfected mutant APP$_{Swe/Ind}$ cDNA into mouse neuroblastoma (N2a) cells for 24 hrs and after transfection, cells were treated with DDQ (250 nM) for 24 hrs. The inventors harvested mutant APP$_{Swe/Ind}$ cells treated and untreated with DDQ and prepared protein lysates and performed co-immunoprecipitation using Aβ (6E10) antibody and conducted immunoblotting analysis with 6E10 and Drp1 antibodies.

The inventors performed co-immunoprecipitation (co-IP) assays using the Dynabeads Kit for Immunoprecipitation (Invitrogen). Briefly, 50 μL of Dynabeads containing protein G was incubated with 10 μg 6E10 or 10 μg of the Drp1 antibodies (both mono- and polyclonal antibodies; Santa Cruz), with rotation, for 1 h at room temperature. The inventors used all the reagents and buffers provided in the kit. Details of antibodies used for co-IP and western blotting are given Table 5. The Dynabeads-Aβ complex was washed three times with a washing buffer and was then incubated overnight with 400 μg of protein at 4° C., with rotation. The incubated Dynabead antigen/antibody complexes were washed again 3 times with a washing buffer, and an immunoprecipitant was eluted from the Dynabeads, using a NuPAGE LDS sample buffer. The Aβ and Drp1 IP elute was loaded onto a 4-20 gradient gel, followed by western blot analysis of Aβ and/or Drp1 antibodies. The inventors also cross-checked the results by performing co-IP experiments, using both anti-Aβ and anti-Drp1 antibodies [10].

TABLE 5

Summary of antibody dilutions and conditions used in the co-immunoprecipitation.

| Co-IP 6E10 and WB with 6E10 | Mouse monoclonal 10 ug/500 ug protein | BioLegend San Diego, CA | WB 6E10 | Mouse Monoclonal 1:500 | BioLegend San Diego, CA | Sheep anti-mouse HRP 1:10,000 | GE Healthcare Amersham, Piscataway, NJ |
|---|---|---|---|---|---|---|---|
| Co-IP 6E10 and WB with Drp1 | Mouse monoclonal 10 ug/500 ug protein | BioLegend San Diego, CA | WB Drp1 | Rabbit Polyclonal 1:400 | Novus Biological, Littleton, CO | Donkey anti-rabbit HRP 1:10,000 | GE Healthcare Amersham, Piscataway, NJ |

Immunofluorescence analysis. To study immune-reactivity of proteins of interest, cells were grown on coverslips using regular cell culture medium and treated as shown in strategy FIG. 3 and performed immunofluorescence analysis using the antibodies in these treated and untreated cells as described by Manzcak et al [13]. Details of proteins, dilutions of antibodies used for immunofluorescence analysis was given in Table 6. Cells were washed with warm PBS, fixed in freshly prepared 4% paraformaldehyde in PBS for 10 min, and then washed with PBS and permeabilized with 0.1% Triton-X100 in PBS. They were blocked with 1% blocking solution (Invitrogen) for 1 hr at room temperature. All neurons were incubated overnight with primary antibodies. The neurons were incubated with appropriate secondary antibodies. The cells were washed neurons 3 times with PBS, and slides were mounted. Photographs were taken with a multiphoton laser scanning microscope system (ZeissMeta LSM510). To quantify the immunoreactivity of proteins of interest, for each treatment 10-15 photographs were taken at ×20 magnification.

TABLE 6

Summary of antibody dilutions and conditions used in the immunohistochemistry/immunofluorescence analysis of Drp1, Synaptophysin and PSD95 in the SHSYSY cell treated with DDQ, Aβ, Aβ + DDQ and DDQ + Aβ.

| Marker | Primary antibody— species and dilution | Purchased from Company, State | Secondary antibody, dilution, Alexa fluor dye | Purchased from Company, City & State |
|---|---|---|---|---|
| Drp1 | Rabbit Polyclonal 1:300 | Novus Biological, Littleton, CO | Goat anti-rabbit Biotin 1:400, HRP-Streptavidin (1:200), TSA-Alexa488 | KPL, Gaithersburg, MD VECTOR Laboratories INC, Burlingame, CA Molecular Probe, Grand Island, NY |
| SYN | Rabbit Polyclonal 1:300 | Protein Tech Group, Inc, Chicago, IL | Goat anti-rabbit Biotin 1:400, HRP-Streptavidin (1:200), TSA-Alexa488 | KPL, Gaithersburg, MD VECTOR Laboratories INC, Burlingame, CA Molecular Probe, Grand Island, NY |
| PSD95 | Rabbit Monoclonal 1:300 | Abcam, Cambridge, MA | Goat anti-rabbit Biotin 1:400, HRP-Streptavidin (1:200), TSA-Alexa594 | KPL, Gaithersburg, MD VECTOR Laboratories INC, Burlingame, CA Molecular Probe, Grand Island, NY |

Double labeling immunofluorescence analysis of Drp1 and Aβ. To determine the interaction between Drp1 and Aβ, the inventors conducted double-labeling immunofluorescence analysis, using an anti-Drp1 antibody (rabbit polyclonal, Santa Cruz Biotechnology) and 6E10 (Covance). As described earlier, the sections from AD patients and control subjects were deparaffinized and treated with sodium borohydrate to reduce autofluorescence.

For the first labeling, the Aβ incubated (DDQ pre-treated, post-treated and untreated) cells were incubated overnight with the anti-Drp1 antibody (1:200) at room temperature. On the day after this primary antibody incubation, the sections were washed with 0.5% Triton in PBS. They were then incubated with a secondary biotinylated anti-rabbit antibody at a 1:400 dilution (Vector Laboratories, Burlingame, Calif., USA) or a secondary biotinylated anti-mouse antibody (1:400) for 1 h at room temperature. They were incubated for 1 h with labeled streptavidin, an HRP solution (Molecular Probes). The cells were washed three times each with PBS for 10 min, at pH 7.4, and treated with Tyramide Alexa488 for 10 min at room temperature.

For the second labeling, the cells were blocked for 1 h with a blocking solution containing 0.5% Triton in PBS+ 10% donkey serum+1% BSA. Then they were incubated overnight with 6E10 (1:200 dilution, Covance) at room temperature. Next, they were incubated with the donkey anti-mouse secondary antibody labeled with Alexa 594 for 1 h at room temperature. They were cover-slipped with Prolong Gold and photographed with a confocal microscope [10].

Transmission electron microscopy. To determine the effects of DDQ on the numbers of mitochondria and any rescue effects of DDQ on mitochondria in the mutant SHSY5Y neurons, the inventors used TEM on untreated and treated SHSY5Y cells (as shown in FIG. 3). [Batches 1-5]. All SHSY5Y cells batches 1-5 were fixed in 100 µm sodium cacodylate (pH 7.2), 2.5% glutaraldehyde, 1.6% paraformaldehyde, 0.064% picric acid and 0.1% ruthenium red. They were gently washed and post-fixed for 1 h in 1% osmium tetroxide plus 08% potassium ferricyanide, in 100 mm sodium cacodylate, pH 7.2. After a thorough rinsing in water, the SHSY5Y cells were dehydrated, infiltrated overnight in 1:1 acetone:Epon 812 and infiltrated for 1 h with 100% Epon 812 resin. They were then embedded in the resin. After polymerization, 60 to 80 nm thin sections were cut on a Reichert ultramicrotome and stained for 5 min in lead citrate. They were rinsed and post-stained for 30 min in uranyl acetate and then were rinsed again and dried. Electron microscopy was performed at 60 kV on a Philips Morgagne TEM equipped with a CCD, and images were collected at magnifications of ×1000-37 000. The numbers of mitochondria were counted in the SHSY5Y cells batches 1-5, and statistical significance was determined, using one-way ANOVA.

Mitochondrial function assays. Hydrogen peroxide production. Using an Amplex® Red $H_2O_2$ Assay Kit (Molecular Probes, Eugene, Oreg.), the inventors measured the production of $H_2O_2$ in independent experiments (n=4) of SHSY5Y neurons treated 1) with and 2) without DDQ, DDQ treated and then incubated with Aβ, as described in Manczak et al. [13].

Cytochrome oxidase activity. Cytochrome oxidase activity was measured in the mitochondria isolated from SHSY5Y cells of control and experimental treatments (n=4), as described in Manczak et al.[33]. Enzyme activity was assayed spectrophotometrically using a Sigma Kit (Sigma-Aldrich) following manufacturer's instructions.

ATP levels. ATP levels were measured in mitochondria isolated from SHSY5Y neurons of control and experimental treatments (n=4) using the ATP determination kit (Molecular Probes) as described in Manczak et al. [13].

Lipid peroxidation assay. Lipid peroxidates are unstable indicators of oxidative stress in neurons. 4-hydroxy-2-nonenol (HNE) is the final product of lipid peroxidation that was measured in the cell lysates from SHSY5Y cells of control and experimental treatments (n=4), using an HNE-His ELISA Kit (Cell BioLabs, Inc., San Diego, Calif.) as described in Manczak et al. [13].

Cell viability test (MTT assay). Mitochondrial respiration, an indicator of cell viability, was assessed in the SHSY5Y cells from control and experimental treatments (n=4), using the mitochondrial-dependent reduction of 3-(4, 5-dimethyl-thiazol-2-yl)-2,5-diphenyl-tetrazolium bromide (MTT) to formazan as described in Manczak et al. [13].

Statistical analyses. Statistical analyses were conducted in 2 ways: 1. untreated cells versus cells treated with Aβ, DDQ, DDQ+Aβ and Aβ+DDQ and 2. Cells treated with Aβ versus DDQ+Aβ and Aβ+DDQ for mRNA and protein levels, cell viability and mitochondrial functional parameters $H_2O_2$, cytochrome oxidase activity, lipid peroxidation, ATP production and cell viability using appropriate statistical analysis.

Huntington's disease. To determine whether Mdivi1 reduces excessive mitochondrial fragmentation and enhances mitochondrial function and synaptic activity in bacterial artificial chromosome transgenic Huntington's disease (BACHD) mice.

The inventors treated BACHD mice and non-transgenic wild-type mice with Mdivi-1 for six months. Behavioral analysis were performed using rotarod (motor coordination), open field (locomotor activity), Y-maze (working memory) and tail suspension (neurological phenotype) in both treated and untreated BACHD and non-transgenic wild-type (WT) mice. The behavioral phenotype significantly improved for all tests in Mdivi-1-treated BACHD mice relative to Mdivi-1-untreated BACHD mice. These observations demonstrate that Mdivi-1 reduces mutant huntingtin-induced behavioral abnormalities in BACHD mice. The inventors also completed studies on the cell and molecular biology aspects of mitochondria and mutant huntingtin experiments. And also completed experiments on mitochondrial morphology (number and length) dendritic spine density in Mdivi-1-treated and untreated BACHD and non-transgenic WT mice.

It was also found that in Mdivi-1-treated BACHD mice relative to Mdivi-1-untreated BACHD mice—1) mRNA and protein levels of fission genes (Drp1 and Fis1) were significantly reduced, 2) mitochondrial fusion genes (Mfn1, Mfn2, and Opa1) were significantly increased, 3) Mitochondrial biogenesis (PGC1a, Nrf1, Nrf2 and TFAM) and synaptic (synaptophysin, PSD95, DARPP32) genes were increased, 4), autophagy (LC3A, LC3B, ATG5, Beclin 1) and mitophagy (PINK1, TERT, BCL2, BNIP3L) genes increased. Mdivi-1-treated BACHD mice had increased dendritic spines in striatal, cortical and hippocampal tissues of Mdivi-1-treated BACHD mice relative Mdivi-1-untreated BACHD mice. Mdivi-1-treated BACHD mice had increased mitochondrial length and reduced the size of mitochondrial size. These observations show that Mdivi-1 reduces mitochondrial fragmentation and enhances synaptic activity.

Impact of MitoQ in Wild-type and Transgenic Tau mice: The inventors investigated the protective effects of MitoQ and daily exercise in 12-month-old transgenic Tau (P301L strain) and age-matched wild-type mice. The purpose of this study was to assess the lifestyle factors (antioxidant-enriched diet) and physical exercise (Treadmill) effects on cognitive behavior and AD pathologies (Abeta, P-tau, mitochondrial and synaptic) in AD mice.

First, the inventors fed wild-type, Tau and APP/PS1 mice with (500 uM of MitoQ in drinking water) and physical exercise (30 minutes on Treadmill) for 3 weeks. The inventors used 12-month-old animals (n=7) per group for all treatments (WT-MitoQ, WT-Treadmill, WT-MitoQ+Treadmill), Tau (Tau-MitoQ, Tau-Treadmill,Tau-MitoQ+Treadmill) and APP/PS1 (APP/PS1-MitoQ, APP/PS1-Treadmill, APP/PS1-MitoQ+Treadmill). Age-matched control mice were used for all genotypes in these studies. After 3-weeks treatment, the cognitive behavior using Morris Water Maze test was assessed.

The inventors conducted 11 trials (4 training and 7 actual) for latency to find the platform for all groups of mice. The results from treadmill exercised WT mice reached platform significantly faster than control WT mice (P=0.0308). MitoQ treated WT mice did not show any significant difference than control WT mice in reaching the platform. However, MitoQ+Treadmill treated WT mice reached significantly faster than control WT mice (P=0.0279). These observations show that combined treatment (MitoQ+Treadmill) is better than single treatment for cognitive function.

Treadmill exercised Tau mice reached platform significantly faster than control Treadmill-unexercised Tau mice (P=0.0286). Interestingly, latency to reach platform is much quicker for MitoQ-treated than control MitoQ untreated Tau mice (P=0.0014). MitoQ+Treadmill (combined treatment) treated Tau mice reached platform significantly faster than MitoQ+Treadmill untreated Tau mice (P=0.0045). These observations show that combined treatment (MitoQ+Treadmill) is better than single treatment.

Similar positive cognitive behavioral data in APP/PS1 mice were obtained for MitoQ, Treadmill and combined treatment. Overall, it was found that MitoQ, Treadmill and combined treatment (MitoQ+Treadmill) of 12-month-old, symptomatic Tau and APP/PS1 mice have improved lifestyle activities on cognitive behavior.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, 35 U.S.C. 112, paragraph (f), or equivalent thereto, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. World Alzheimer Report 2015: The Global Impact of Dementia.
2. Mattson M P (2004) Pathways towards and away from Alzheimer's disease. Nature. 430, 631-639.
3. LaFerla F M, Green K N, Oddo S (2007) Intracellular amyloid-beta in Alzheimer's disease. Nat Rev Neurosci. 8, 499-509.
4. Selkoe D J. (2001) Alzheimer's disease: genes, proteins, and therapy. Physiol Rev. 81, 741-766.
5. Du H, Guo L, Yan S, Sosunov A A, McKhann G M, Yan S S (2010) Early deficits in synaptic mitochondria in an Alzheimer's disease mouse model. Proc Natl Acad Sci USA. 107, 18670-18675.
6. Reddy P. H., Tripathi R., Troung Q., Tirumala K., Reddy T. P., Anekonda V., Shirendeb U. P., Calkins M. J., Reddy A. P., Mao P., Manczak M (2012) Abnormal mitochondrial dynamics and synaptic degeneration as early events in Alzheimer's disease: implications to mitochondria-targeted antioxidant therapeutics. Biochim. Biophys. Acta, 1822, 639-649.
7. Zhu Z, Yan J, Jiang W, Yao X G, Chen J, Chen L, Li C, Hu L, Jiang H, Shen X. (2013) Arctigenin effectively ameliorates memory impairment in Alzheimer's disease model mice targeting both β-amyloid production and clearance. J Neurosci. 33, 13138-13149.
8. Reddy P H. (2011) Abnormal tau, mitochondrial dysfunction, impaired axonal transport of mitochondria, and synaptic deprivation in Alzheimer's disease. Brain Res. 1415, 136-148.
9. Reddy P H, Manczak M, Mao P, Calkins M J, Reddy A P, Shirendeb U. (2010) Amyloid-beta and mitochondria in aging and Alzheimer's disease: implications for synaptic damage and cognitive decline. J Alzheimers Dis. 20, S499-512.
10. Manczak M., Calkins M J and Reddy P. H (2011) Impaired mitochondrial dynamics and abnormal interaction of amyloid beta with mitochondrial protein Drp1 in neurons from patients with Alzheimer's disease: implications for neuronal damage. Hum Mol Genet. 20, 2495-2509.
11. Manczak M, Reddy P H (2012) Abnormal interaction of VDAC1 with amyloid beta and phosphorylated tau causes mitochondrial dysfunction in Alzheimer's disease. Hum Mol Genet. 21, 5131-5146.
12. Manczak M, Reddy P H (2012) Abnormal interaction between the mitochondrial fission protein Drp1 and hyperphosphorylated tau in Alzheimer's disease neurons: implications for mitochondrial dysfunction and neuronal damage. Hum Mol Genet. 21, 2538-2547.
13. Manczak M, Kandimalla R, Fry D, Sesaki H, Reddy P H (2016) Protective effects of reduced dynamin-related protein 1 against amyloid beta-induced mitochondrial dysfunction and synaptic damage in Alzheimer's disease. Hum Mol Genet. Hum Mol Genet 25, 5148-5166.
14. Kandimalla R, Manczak M, Fry D, Suneetha Y, Sesaki H, Reddy P H (2016) Reduced dynamin-related protein 1 protects against phosphorylated Tau-induced mitochondrial dysfunction and synaptic damage in Alzheimer's disease. Hum Mol Genet. 25, 4881-4897.
15. Reddy P H, Beal M F (2008) Amyloid beta, mitochondrial dysfunction and synaptic damage: implications for cognitive decline in aging and Alzheimer's disease. Trends Mol Med. 14, 45-53.
16. Lustbader J W, Cirilli M, Lin C, Xu H W, Takuma K, Wang N, Caspersen C, Chen X, Pollak S, Chaney M, Trinchese F, Liu S, Gunn-Moore F, Lue L F, Walker D G, Kuppusamy P, Zewier Z L, Arancio O, Stern D, Yan S S, Wu H (2004) ABAD directly links Abeta to mitochondrial toxicity in Alzheimer's disease. Science. 304, 448-452.
17. Manczak M, Anekonda T S, Henson E, Park B S, Quinn J, Reddy P H (2006) Mitochondria are a direct site of A beta accumulation in Alzheimer's disease neurons: implications for free radical generation and oxidative damage in disease progression. Hum Mol Genet. 15, 1437-1449.

18. Devi L, Prabhu B M, Galati D F, Avadhani N G, Anandatheerthavarada H K (2006) Accumulation of amyloid precursor protein in the mitochondrial import channels of human Alzheimer's disease brain is associated with mitochondrial dysfunction. J. Neurosci. 26, 9057-9068.
19. Yao J, Irwin R W, Zhao L, Nilsen J, Hamilton R T, Brinton R D (2009) Mitochondrial bioenergetic deficit precedes Alzheimer's pathology in female mouse model of Alzheimer's disease. Proc Natl Acad Sci USA. 106, 14670-14675.
20. Hansson Petersen C A, Alikhani N, Behbahani H, Wiehager B, Pavlov P F, Alafuzoff I, Leinonen V, Ito A, Winblad B, Glaser E, Ankarcrona M (2008) The amyloid beta-peptide is imported into mitochondria via the TOM import machinery and localized to mitochondrial cristae. Proc Natl Acad Sci USA. 105, 13145-13150.
21. Caspersen C, Wang N, Yao J, Sosunov A, Chen X, Lustbader J W, Xu H W, Stern D, McKhann G, Yan S D (2005) Mitochondrial Abeta: a potential focal point for neuronal metabolic dysfunction in Alzheimer's disease. FASEB J. 19, 2040-2041.
22. Du H, Guo L, Fang F, Chen D, Sosunov A A, McKhann G M, Yan Y, Wang C, Zhang H, Molkentin J D, et al (2008) Cyclophilin D deficiency attenuates mitochondrial and neuronal perturbation and ameliorates learning and memory in Alzheimer's disease. Nat. Med. 14, 1097-1105.
23. Reddy P H (2009) Amyloid beta, mitochondrial structural and functional dynamics in Alzheimer's disease. Exp Neurol. 218, 286-292.
24. Du H, Guo L, Yan S S (2012) Synaptic mitochondrial pathology in Alzheimer's disease. Antioxid Redox Signal. 16, 1467-1475.
25. Sheng J H, Ng T P, Li C B, Lu G H, He W, Qian Y P, Wang J H, Yu S Y (2012) The peripheral messenger RNA expression of glycogen synthase kinase-3β genes in Alzheimer's disease patients: a preliminary study. Psychogeriatrics. 12, 248-254.
26. Reddy P H (2006) Amyloid precursor protein-mediated free radicals and oxidative damage: implications for the development and progression of Alzheimer's disease. J Neurochem. 96, 1-13.
27. Swerdlow R H, Burns J M, Khan S M (2010) The Alzheimer's disease mitochondrial cascade hypothesis. J Alzheimers Dis. 20 Suppl 2:S265-279.
28. Maria Manczak, Peizhong Mao, Marcus Calkins, Anda Cornea, Arubula Reddy, Michael Murphy, Hazel Szeto, Byung Park, Hemachandra Reddy. (2010) Mitochondria-targeted antioxidants protect against amyloid-beta toxicity in Alzheimer's disease neurons. J. Alzheimers Dis., 20(Suppl. 2), S609-S631.
29. Marcus Calkins, Maria Manczak, Peizhong Mao, Ulziibat Shirendeb, Hemachandra Reddy. (2011) Impaired mitochondrial biogenesis, defective axonal transport of mitochondria, abnormal mitochondrial dynamics and synaptic degeneration in a mouse model of Alzheimer's disease. Hum. Mol. Genet., 20, 4515-4529.
30. Swerdlow, R H (2012) Mitochondria and cell bioenergetics: increasingly recognized components and a possible etiologic cause of Alzheimer's disease. Antioxid Redox Signal. 16, 1434-1455.
31. Wang X., Su B., Lee H. G., Li X., Perry G., Smith M. A., Zhu X (2009) Impaired balance of mitochondrial fission and fusion in Alzheimer's disease. J. Neurosci. 29, 9090-9103.
32. Xinglong Wang, Bo Su, Sandra Siedlak, Paula Moreira, Hisashi Fujioka, Yang Wang, Gemma Casadesus, Xiongwei Zhu. (2008) Amyloid-beta overproduction causes abnormal mitochondrial dynamics via differential modulation of mitochondrial fission/fusion proteins. Proc. Natl. Acad. Sci. USA., 105, 19318-19323.
33. Zheng Li, Ken-Ichi Okamoto, Yasunori Hayashi, Morgan Sheng. (2004) The importance of dendritic mitochondria in the morphogenesis and plasticity of spines and synapses. Cell. 119(6):873-87.
34. Reddy P H, Reddy T P, Manczak M, Calkins M J, Shirendeb U, Mao P (2011) Dynamin-related protein 1 and mitochondrial fragmentation in neurodegenerative diseases. Brain Res Rev. 67, 103-118.
35. Kandimalla R, Reddy P H. (2016) Multiple faces of dynamin-related protein 1 and its role in Alzheimer's disease pathogenesis. Biochim Biophys Acta. 1862, 814-828.
36. Gouras G K, Tsai J, Naslund J, Vincent B, Edgar M, Checler F, Greenfield J P, Haroutunian V, Buxbaum J D, Xu H, Greengard P, Relkin N R (2000) Intraneuronal Abeta-42 accumulation in human brain. Am J Pathol. 156, 15-20.
37. Gouras G. K., Almeid C. G., Takahashi R. H (2005) Intraneuronal Abeta accumulation and origin of plaques in Alzheimer's disease. Neurobiol. Aging. 26, 1235-1244.
38. Gouras G K, Tampellini D, Takahashi R H, Capetillo-Zarate E. (2010) Intraneuronal beta-amyloid accumulation and synapse pathology in Alzheimer's disease. Acta Neuropathol. 119, 523-541.
39. Cassidy-Stone A, Chipuk J E, Ingerman E, Song C, Yoo C, Kuwana T, Kurth M J, Shaw J T, Hinshaw J E, Green D R, Nunnari J. (2008) Chemical inhibition of the mitochondrial division dynamin reveals its role in Bax/Bak-dependent mitochondrial outer membrane permeabilization. Dev Cell. 14, 193-204.
40. Macia E, Ehrlich M, Massol R, Boucrot E, Brunner C, Kirchhausen T (2006) Dynasore, a cell-permeable inhibitor of dynamin. Dev Cell. 10, 839-850.
41. Reddy P H, Manczak M and Yin (2017) Mitochondria-Division Inhibitor 1 Protects Against Amyloid-β induced Mitochondrial Fragmentation and Synaptic Damage in Alzheimer's Disease J Alzheimer Dis (in press)
42. Reddy P H, Manczak and Kandimalla (2017) Mitochondria-targeted small molecule SS31: a potential candidate for the treatment of Alzheimer's disease. Hum Mol Genet doi: 10.1093/hmg/ddx052, Advance Access Publication Date: 10 Feb. 2017.
43. Kuruva C S, Reddy P H, (2017) Amyloid beta modulators and neuroprotection in Alzheimer's disease: a critical appraisal, Drug Discov Today. 2, 223-233.
44. Kacprzak V, Patel N A, Riley E, Yu L, Yeh J J, Zhdanova I V. Dopaminergic control of anxiety in young and aged zebrafish. Pharmacol Biochem Behav. 2017 Apr. 10. pii: S0091-3057(16)30212-X.
45. Molecular Operating Environment (MOE) (2011).10; Chemical Computing Group Inc., 1010 Sherbooke St. West, Suite #910, Montreal, QC, Canada, H3A 2R7, 2011.
46. Kuruva K C, Avilala J, Kumar Y N, Golla N, Chamarthi N, Ghosh S K. (2014) Amino acid esters substituted phosphorylated emtricitabine and didanosine derivatives as antiviral and anticancer agents. Appl Biochem Biotechnol. 173, 1303-1318.
47. Ordonez M, Rojas-Cabrera H, Cativiela C (2009) An overview of stereoselective synthesis of α-aminophosphonic acids and derivatives. Tetrahedron. 65, 17-49.
48. Li Y J, Wang C Y, Ye M Y, Yao G Y, Wang H S (2015) Novel Coumarin-Containing Aminophosphonatesas Antitumor Agent: Synthesis, Cytotoxicity, DNA-Binding and Apoptosis Evaluation. Molecules. 20, 14791-14809.

What is claimed is:

1. A method of inhibiting an interaction between Aβ and Drp1 proteins in nerve cells comprising: providing diethyl (3,4-dihydroxyphenethylamine)(quinolin-4-yl)methylphosphonate (DDQ) in an amount that inhibits the interaction of Aβ and Drp1 proteins in nerve cells.

2. The method of claim 1, wherein the DDQ inhibits mitochondrial, intracellular, and extracellular damage caused by the interaction of Aβ and Drp1 in or about the nerve cells.

3. The method of claim 1, wherein the DDQ is formulated for oral, intravenous, intramuscular, intraperitoneal, subcutaneous, parenteral, or pulmonary administration.

4. The method of claim 1, wherein the Aβ and Drp1 proteins are human.

5. The method of claim 1, wherein the DDQ delays age-dependent disease process in Alzheimer's, Huntington's, Parkinson's, or ALS.

6. The method of claim 1, wherein the DDQ increases dendritic spines in striatal, cortical and hippocampal tissues.

7. The method of claim 1, wherein the DQQ delays aging in neurons; protects neurons from oxidative insults.

8. The method of claim 1, wherein the DQQ inhibits abnormal protein-protein interactions, protect neurons from mutant protein(s)-induced toxicities.

9. The method of claim 1, wherein the DQQ enhances nerve cell survival.

10. The method of claim 1, wherein the DQQ reduces mRNA and protein levels of fission genes (Drp1 and/or Fis1).

11. The method of claim 1, wherein the DQQ increases the expression of mitochondrial fusion genes (Mfn1, Mfn2, and/or Opa1).

12. The method of claim 1, wherein the DQQ increased the expression of mitochondrial biogenesis (PGC1a, Nrf1, Nrf2 and/or TFAM) and synaptic (synaptophysin, PSD95, and/or DARPP32) genes.

13. The method of claim 1, wherein the DQQ increases autophagy (LC3A, LC3B, ATG5, and/or Beclin 1) and mitophagy (PINK1, TERT, BCL2, and/or BNIP3L) genes.

* * * * *

SEQUENCE LISTING

<160> NUMBER OF SEQ ID NOS: 38

<210> SEQ ID NO 1
<211> LENGTH: 15
<212> TYPE: DNA
<213> ORGANISM: Artificial Sequence
<220> FEATURE:
<223> OTHER INFORMATION: Synthetic primer

<400> SEQUENCE: 1
tgggcgccga catca                                                    15

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gctctgcgtt cccactacga                                               20

<210> SEQ ID NO 3
<211> LENGTH: 17
<212> TYPE: DNA
<213> ORGANISM: Artificial Sequence
<220> FEATURE:
<223> OTHER INFORMATION: Synthetic primer

<400> SEQUENCE: 3
tacgtccgcg ggttgct                                                  17

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
ccagttcctt ggcctggtt                                                19

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
tctccaagcc caacatcttc a                                             21

<210> SEQ ID NO 6
<211> LENGTH: 17
<212> TYPE: DNA
<213> ORGANISM: Artificial Sequence
<220> FEATURE:
<223> OTHER INFORMATION: Synthetic primer

<400> SEQUENCE: 6
actccggctc cgaagca                                                  17

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tggtgaggtg ctatctcgga                                        20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
aacagagctc ttcccactgc                                        20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
cattcaggct gcaccaagtg                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
tggtagtgcc ccctttaacg                                        20

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
ggacattcag gcgcacaag                                         19

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tcccgtagag gtggctgttg                                        20

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
tgaggacatc agtgtcgggt aa                                     22

```
<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ggcaatctgc tcaagcatag c                                              21

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
tcccactcat tgagcagaca tact                                           24

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
gggaacgtag gaagcgtaag c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
tgctgccaag ctaaaaagga a                                              21

<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
cagatagctc ccagcatgat ca                                             22

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
cggaagagtc agtctccatt gg                                             22

<210> SEQ ID NO 20
<211> LENGTH: 23
<212> TYPE: DNA
<213> ORGANISM: Artificial Sequence
<220> FEATURE:
<223> OTHER INFORMATION: Synthetic primer
```

-continued

<400> SEQUENCE: 20
cacctgcaga taatgtcgtg cta                                      23

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
agccggacga cgacattcta                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
aaactcgcct ggattttggc                                          20

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
ctgaggagga gaaagacgct gta                                      23

<210> SEQ ID NO 24
<211> LENGTH: 18
<212> TYPE: DNA
<213> ORGANISM: Artificial Sequence
<220> FEATURE:
<223> OTHER INFORMATION: Synthetic primer

<400> SEQUENCE: 24
tcctgtcggg cactttcc                                            18

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
tcctgcgccc tgaaccta                                            18

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gacgggcgac agagcataga                                          20

<210> SEQ ID NO 27

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 27
ttcccgttca gctctggg                                                   18

<210> SEQ ID NO 28
<211> LENGTH: 18
<212> TYPE: DNA
<213> ORGANISM: Artificial Sequence
<220> FEATURE:
<223> OTHER INFORMATION: Synthetic primer

<400> SEQUENCE: 28
ccctgcatcc actggtgc                                                   18

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
gcagtcgcaa catgctcaag                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30 gggaacccttt ggggtcattt                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
agaaacggaa acggcctcat                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
catccaacgt ggctctgagt                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
```

```
atggagcaag tttggcagga                                           20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
gctgggaaca gcggtagtat                                           20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
tccacagaac agctacccaa                                           20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
ccacagggct gcaattttcc                                           20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
agacctgtac gccaacacag                                           20

<210> SEQ ID NO 38
<211> LENGTH: 19
<212> TYPE: DNA
<213> ORGANISM: Artificial Sequence
<220> FEATURE:
<223> OTHER INFORMATION: Synthetic primer

<400> SEQUENCE: 38
tctgcatcct gtcggcaat                                            19
```